US009999721B2

(12) United States Patent
Chow et al.

(10) Patent No.: US 9,999,721 B2
(45) Date of Patent: Jun. 19, 2018

(54) ERROR HANDLING IN INFUSION DEVICES WITH DISTRIBUTED MOTOR CONTROL AND RELATED OPERATING METHODS

(71) Applicant: MEDTRONIC MINIMED, INC., Northridge, CA (US)

(72) Inventors: Steve Chow, Northridge, CA (US); Alexander S. Campbell, Tarzana, CA (US); Yongbo Wang, Arcadia, CA (US); Thomas W. Collins, Palos Verdes Estates, CA (US); Linda I. Torres, Moorpark, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 146 days.

(21) Appl. No.: 14/721,807

(22) Filed: May 26, 2015

(65) Prior Publication Data
US 2016/0346459 A1    Dec. 1, 2016

(51) Int. Cl.
*A61M 5/145*    (2006.01)
*A61M 5/168*    (2006.01)
(Continued)

(52) U.S. Cl.
CPC .......... *A61M 5/145* (2013.01); *A61M 5/1452* (2013.01); *A61M 5/16831* (2013.01);
(Continued)

(58) Field of Classification Search
CPC .............. A61M 5/145; A61M 5/16831; A61M 5/1452; A61M 2005/14208;
(Continued)

(56) References Cited

U.S. PATENT DOCUMENTS 3,631,847 A    1/1972  Hobbs, II
4,212,738 A    7/1980  Henne
(Continued)

FOREIGN PATENT DOCUMENTS

DE    4329229    3/1995
EP    0319268    11/1988
(Continued)

OTHER PUBLICATIONS

PCT Search Report for (PCT/US02/03299), dated Oct. 31, 2002, Medtronic Minimed, Inc.
(Continued)

*Primary Examiner* — Lauren P Farrar
(74) *Attorney, Agent, or Firm* — Lorenz & Kopf, LLP

(57) ABSTRACT

Infusion systems, infusion devices, and related operating methods are provided. An exemplary infusion device includes a motor operable to deliver fluid to a body of a user, a first control module to enable input power for the motor and provide a dosage command for operating the motor, and a second control module coupled to the first control module to receive the dosage command and operate the motor using at least a portion of the input power based at least in part on the dosage command. One of the first control module and the second control module detects an anomalous condition, and in response, disables the input power to the motor, stores diagnostic information for the anomalous condition in its internal memory, and automatically resets thereafter.

19 Claims, 9 Drawing Sheets

(51) Int. Cl.
    *A61M 5/142*       (2006.01)
    *G06F 19/00*       (2018.01)
(52) U.S. Cl.
    CPC .............. *G06F 19/3468* (2013.01); *A61M 2005/14208* (2013.01); *A61M 2205/3569* (2013.01); *A61M 2205/6018* (2013.01)
(58) Field of Classification Search
    CPC .. A61M 2205/6018; A61M 2205/3569; A61M 2005/16863; G06F 19/3468
    See application file for complete search history.

(56) References Cited

U.S. PATENT DOCUMENTS

| | | |
|---|---|---|
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | Decant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,505,709 A | 4/1996 | Funderburk et al. |
| 5,497,772 A | 5/1996 | Schulman et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Iliff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A * | 8/1999 | Peterson .............. G09B 19/003 604/65 |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,248,093 B1 | 6/2001 | Moberg |
| 6,259,937 B1 | 7/2001 | Schulman et al. |

(56) References Cited

U.S. PATENT DOCUMENTS

| | | |
|---|---|---|
| 1,004,473 A1 | 11/2001 | Coffman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,589,229 B1 | 7/2003 | Connelly et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,740,072 B2 | 5/2004 | Starkweather et al. |
| 6,746,582 B2 | 6/2004 | Heller et al. |
| 6,747,556 B2 | 6/2004 | Medema et al. |
| 6,749,740 B2 | 6/2004 | Llamos et al. |
| 6,752,787 B1 | 6/2004 | Causey, III et al. |
| 6,809,653 B1 | 10/2004 | Mann et al. |
| 6,817,990 B2 | 11/2004 | Yap et al. |
| 6,827,702 B2 | 12/2004 | Lebel et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,323,142 B2 | 1/2008 | Pendo et al. |
| 7,396,330 B2 | 7/2008 | Banet et al. |
| 7,402,153 B2 | 7/2008 | Steil et al. |
| 7,621,893 B2 | 11/2009 | Moberg et al. |
| 8,474,332 B2 | 7/2013 | Bente, IV |
| 8,523,803 B1 | 9/2013 | Favreau |
| 8,603,026 B2 | 12/2013 | Favreau |
| 8,603,027 B2 | 12/2013 | Favreau |
| 8,674,288 B2 | 3/2014 | Hanson et al. |
| 2002/0013518 A1* | 1/2002 | West ............... A61B 5/1113 600/300 |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0173444 A1* | 8/2006 | Choy ............... A61M 5/172 604/891.1 |
| 2006/0184154 A1* | 8/2006 | Moberg ............ A61M 5/14566 604/506 |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0154503 A1 | 6/2008 | Wittenber et al. |
| 2009/0081951 A1 | 3/2009 | Erdmann et al. |
| 2009/0082635 A1 | 3/2009 | Baldus et al. |
| 2013/0253420 A1* | 9/2013 | Favreau ............ F04B 49/10 604/67 |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |

OTHER PUBLICATIONS (Animas Corporation, 1999). Animas . . . bringing new life to insulin therapy.

Bode B W, et al. (1996). Reduction in Severe Hypoglycemia with Long-Term Continuous Subcutaneous Insulin Infusion in Type I Diabetes. Diabetes Care, vol. 19, No. 4, 324-327.

Boland E (1998). Teens Pumping it Up! Insulin Pump Therapy Guide for Adolescents. 2nd Edition.

Brackenridge B P (1992). Carbohydrate Gram Counting a Key to Accurate Mealtime Boluses in Intensive Diabetes Therapy. Practical Diabetology, vol. 11, No. 2, pp. 22-28.

Brackenridge, B P et al. (1995). Counting Carbohydrates How to Zero in on Good Control. MiniMed Technologies Inc.

(56) References Cited

OTHER PUBLICATIONS

Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.
Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting a Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an insulin Pump. Published by MiniMed•Technologies.
(Intensive Diabetes Management, 1995). Insulin Infusion Pump Therapy. pp. 66-78.
Disetronic My Choice™ D-TRON™ Insulin Pump Reference Manual. (no date).
Disetronic H-TRON® plus Quick Start Manual. (no date).
Disetronic My Choice H-TRONplus Insulin Pump Reference Manual. (no date).
Disetronic H-TRON®plus Reference Manual. (no date).
(MiniMed, 1996). The MiniMed 506. 7 pages Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages Retrieved on Sep. 16, 2003 from the World Wide Web: http://web.archive.org/web/19970124234841/www.minimed.com/files/mmn075.htm.
(MiniMed, 1996). FAQ: The Practical Things ... pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump a Tradition of Excellence.
(Medtronic MiniMed, 2002). Medtronic MiniMed Meal Bolus Calculator and Correction Bolus Calculator, International Version.
Abel, P., et al., "Experience with an implantable glucose sensor as a prerequiste of an artificial beta cell," Biomed. Biochim. Acta 43 (1984) 5, pp. 577-584.

Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B, 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International

(56) References Cited

OTHER PUBLICATIONS

Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.
Nishida, Kenro, et al., "Clinical applications of teh wearable artifical endocrine pancreas with the newly designed needle-type glucose sensor," Elsevier Sciences B.V., 1994, pp. 353-358.
Nishida, Kenro, et al., "Development of a ferrocene-mediated needle-type glucose sensor covereed with newly designd biocompatible membrane, 2-methacryloyloxyethylphosphorylcholine-co-n-butyl
nethacrylate," Medical Progress Through Technology, vol. 21, 1995, pp. 91-103.
Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.
Reach, G., "A Method for Evaluating in vivo the Functional Characteristics of Glucose Sensors," Biosensors 2, 1986, pp. 211-220.
Shaw, G. W., et al., "In vitro testing of a simply constructed, highly stable glucose sensor suitable for implantation in diabetic patients," Biosensors & Bioelectronics 6, 1991, pp. 401-406.
Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Aipbach-Innsbruck, Austria, Sep. 1984, pp. 7-9.
Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.
Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.
Shichiri, Motoaki, et al., "Glycaemic Control in a Pacreatectomized Dogs with a Wearable Artificial Endocrine Pancreas," Diabetologia, vol. 24, 1983, pp. 179-184.
Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.
Shichiri, M., et al., "Membrane design for extending the long-life of an implantable glucose sensor," Diab. Nutr. Metab., vol. 2, No. 4, 1989, pp. 309-313.
Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.
Shichiri, Motoaki, et al., "Telemetry Glucose Monitoring Device with Needle-Type Glucose Sensor: A useful Tool for Blood Glucose Monitoring in Diabetic individuals," Diabetes Care, vol. 9, No. 3, May-Jun. 1986, pp. 298-301.
Shichiri, Motoaki, et al., "Wearable Artificial Endocrine Pancreas with Needle-Type Glucose Sensor," The Lancet, Nov. 20, 1982, pp. 1129-1131.
Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.
Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.
Shults, Mark C., "A Telemetry-instrumentation System for Monitoring Multiple Subcutaneously Implanted Glucose Sensors," IEEE Transactions on Biomedical Engineering, vol. 41, No. 10, Oct. 1994, pp. 937-942.
Sternberg, Robert, et al., "Study and Development of Multilayer Needle-type Enzyme-based Glucose Microsensors," Biosensors, vol. 4, 1988, pp. 27-40.
Tamiya, E., et al., "Micro Glucose Sensors using Electron Mediators Immobilized on a Polypyrrole-Modified Electrode," Sensors and Actuators, vol. 18, 1989, pp. 297-307.
Tsukagoshi, Kazuhiko, et al., "Specific Complexation with Mono- and Disaccharides that can be Detected by Circular Dichroism," J. Org. Chem., vol. 56, 1991, pp. 4089-4091.
Urban, G., et al., "Miniaturized multi-enzyme biosensors integrated with pH sensors on flexible polymer carriers for in vivo applciations," Biosensors & Bioelectronics, vol. 7, 1992, pp. 733-739.
Ubran, G., et al., "Miniaturized thin-film biosensors using covalently immobilized glucose oxidase," Biosensors & Bioelectronics, vol. 6, 1991, pp. 555-562.
Velho, G., et al., "In vivo calibration of a subcutaneous glucose sensor for determination of subcutaneous glucose kinetics," Diab. Nutr. Metab., vol. 3, 1988, pp. 227-233.
Wang, Joseph, et al., "Needle-Type Dual Microsensor for the Simultaneous Monitoring of Glucose and Insulin," Analytical Chemistry, vol. 73, 2001, pp. 844-847.
Yamasaki, Yoshimitsu, et al., "Direct Measurement of Whole Blood Glucose by a Needle-Type Sensor," Clinics Chimica Acta, vol. 93, 1989, pp. 93-98.
Yokoyama, K., "Integrated Biosensor for Glucose and Galactose," Analytica Chimica Acta, vol. 218, 1989, pp. 137-142.

\* cited by examiner

US 9,999,721 B2

ERROR HANDLING IN INFUSION DEVICES WITH DISTRIBUTED MOTOR CONTROL AND RELATED OPERATING METHODS

TECHNICAL FIELD

Embodiments of the subject matter described herein relate generally to medical devices, and more particularly, embodiments of the subject matter relate to fluid infusion devices with distributed motor control.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics.

Continuous insulin infusion provides greater control of a diabetic's condition, and hence, control schemes have been developed that allow insulin infusion pumps to monitor and regulate a user's blood glucose level in a substantially continuous and autonomous manner. For example, an insulin infusion pump may operate in a closed-loop operating mode overnight while a user is sleeping to regulate the user's glucose level to a target glucose level. However, care must be taken to avoid potentially compromising a user's condition and ensure compliance with applicable regulatory requirements in the event of software errors or other unpredictable or anomalous operating conditions.

BRIEF SUMMARY

Infusion devices, systems and related methods of operation are provided. One exemplary infusion device includes a motor operable to deliver fluid to a body of a user, a first control module to enable input power for the motor and provide a dosage command for operating the motor, and a second control module coupled to the first control module to receive the dosage command and operate the motor using at least a portion of the input power based at least in part on the dosage command. One of the first control module and the second control module detects an anomalous condition, and in response to the anomalous condition, disables the input power to the motor, stores diagnostic information for the anomalous condition in its internal memory, and resets after disabling the input power and storing the diagnostic information.

In another embodiment, a method of operating a motor of an infusion device to deliver fluid utilizes a first control module and a second control module. The first control module generates one or more dosage commands and the second control module converts the one or more dosage commands to corresponding one or more motor commands for providing input power to the motor. The method involves communicating one or more heartbeat messages between the first control module and the second control module. In response to one of the first control module and the second control module detecting an absence of a heartbeat message of the one or more heartbeat messages, the one of the first control module and the second control module disables the input power to the motor, stores diagnostic information from its processing core to its internal memory, and after storing the diagnostic information, loads boot loader code from its internal memory to its processing core.

An embodiment of a method of operating a motor using a first control module and a second control module is also provided. The method involves initializing each of the first control module and the second control module to a boot loader stage. In response to a first handshake between the first control module and the second control module while in the boot loader stage, the method continues by loading a respective operating system for execution by each of the first control module and the second control module. In response to a second handshake between the respective operating systems executing on the first control module and the second control module, the method continues by loading respective application code for execution by each of the first control module and the second control module from external memory.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
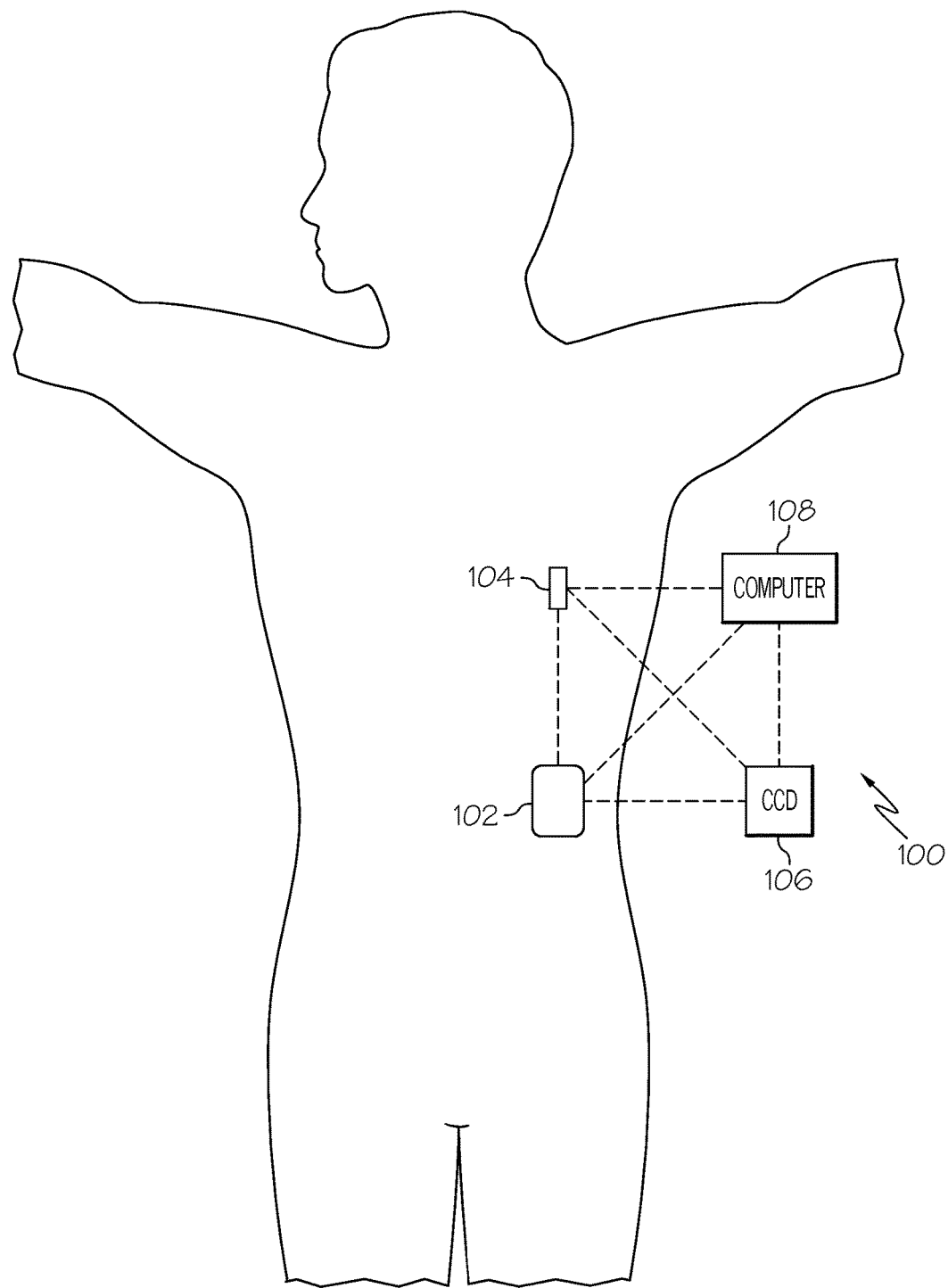
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the subject matter described herein can be implemented in any electronic device that includes a motor, exemplary embodiments described below are implemented in the form of medical devices, such as portable electronic medical devices. Although many different applications are possible, the following description focuses on a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Embodiments of the subject matter described herein generally relate to fluid infusion devices including a motor that is operable to displace a plunger (or stopper) of a reservoir provided within the fluid infusion device to deliver a dosage of fluid, such as insulin, to the body of a patient. The control of the motor is distributed across multiple control modules of the infusion device using handshaking communications sequences in a manner that reduces the likelihood of overdelivery or undetected underdelivery in the event of an erroneous or anomalous condition with respect to any one of the control modules. In this regard, either control module is capable of unilaterally disconnecting or otherwise disabling input power to the motor based on a failure to receive a communication from the other control module that is prescribed by the handshaking communications sequence within an applicable time limit, thereby mitigating the impact on fluid delivery that could otherwise result from an anomalous condition of the other control module.

As described in greater detail below in the context of FIGS. 6-9, either control module is capable of detecting or otherwise identifying an erroneous or anomalous condition with respect to software executing thereon, and in response, the control module automatically and autonomously disables the input power to the motor and stores diagnostic information for the anomalous condition. The anomalous condition may be any sort of unexpected runtime error that cannot be mitigated deterministically, such as, for example, an unexpected software interrupt, corrupted memory, or the like. In one or more embodiments, the anomalous condition may be an inter-processor communication error, a nondestructive memory test failure, a stack corruption, a nonresponsive software task, a cyclic redundancy check (CRC) test failure, a hardware test failure or other hardware error, corrupted user settings, an external interrupt from an unknown source, a software error (e.g., an out of range input value), a power deadlock error, an error while writing to memory, or the like. In one embodiment, the anomalous condition is realized as a critical variable error that is detected when the value of a delivery variable (e.g., an amount of insulin) compared to its inverse value does not sum to zero (e.g., an inverse check failure).

As described in greater detail below, the diagnostic information corresponding to the anomalous condition indicates the current status of the software operating environment at the time of the anomalous condition, such as, for example, the line-of-execution that resulted in the error (e.g., the current execution line number), the data or values stored in registers of the control module, the current call stack, and the like. After storing the diagnostic information and disabling the motor input power, the control module automatically resets itself, for example, by loading and executing boot loader code.

Upon the self-reset, the boot loader of the control module performs initialization self-diagnostic checks or tests (e.g., power-on self-tests) and verifies the performance capabilities of the control module before performing a handshake with the other control module while both control modules are concurrently in the boot loader stage. At the boot loader stage, one of the control modules verifies that the number of anomalous conditions or runtime errors that have been detected does not exceed an allowed limit before proceeding with the handshaking and reloading the operating system and overlying applications supported by the control module. When the error limit has been met, the boot loader generates or otherwise provides a user notification or alert indicating that the control module requires maintenance or other attention. Otherwise, after the operating system is loaded, a user notification or alert may be generated or otherwise provide that identifies, to the user, that the infusion device has recovered from an error and provide other notification information to pertaining to the error (e.g., the type of error, or the like), which, in turn may be based on the stored diagnostic information corresponding to the anomalous condition. In a similar manner, at the operating system stage, the other control module redundantly verifies that the number of anomalous conditions or runtime errors that have been detected does not exceed an allowed limit before performing a handshake with the operating system executing on the first control module while both control modules are concurrently in the operating system stage before loading the overlying complex application(s).

In one or embodiments, one or more communications sequences between the control modules may be configured or otherwise implemented in a manner such that resetting of a first control module of the infusion device results in a second control module of the infusion device also resetting to ensure both control modules of the infusion device are operating in known, safe operating states. For example, during execution of complex software, the underlying operating systems on the control modules may be configured to periodically communicate via heartbeat messages, acknowledgments, or the like that indicate to one another that the control module is functioning normally. Thus, in the absence of a heartbeat message from the operating system of one control module, the other control module may automatically initiate a self-reset. The boot loaders on the control modules may be configured to require handshaking with the boot loader of the other control module before loading its respective operating system, thereby ensuring that both control modules have been reset to the known, safe boot loader state before proceeding with loading the operating systems and more complex applications on the respective control modules. Thus, the infusion device may safely recover and resume normal operation in the event of an unexpected or unpredictable runtime error.

FIG. 1 depicts one exemplary embodiment of an infusion system 100, which includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other agent into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a physiological condition in the body of the user, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106 and/or the computer 108. In such embodiments, the sensing arrangement 104 may be configured to receive a biological sample, analyte, or the like, to measure a condition of the user.

As described above, in some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the patient's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589, 229, 6,740,072, 6,827,702, 7,323,142, and 7,402, 153, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid substantially continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example, only when the user is asleep or awake.

Figure 2:
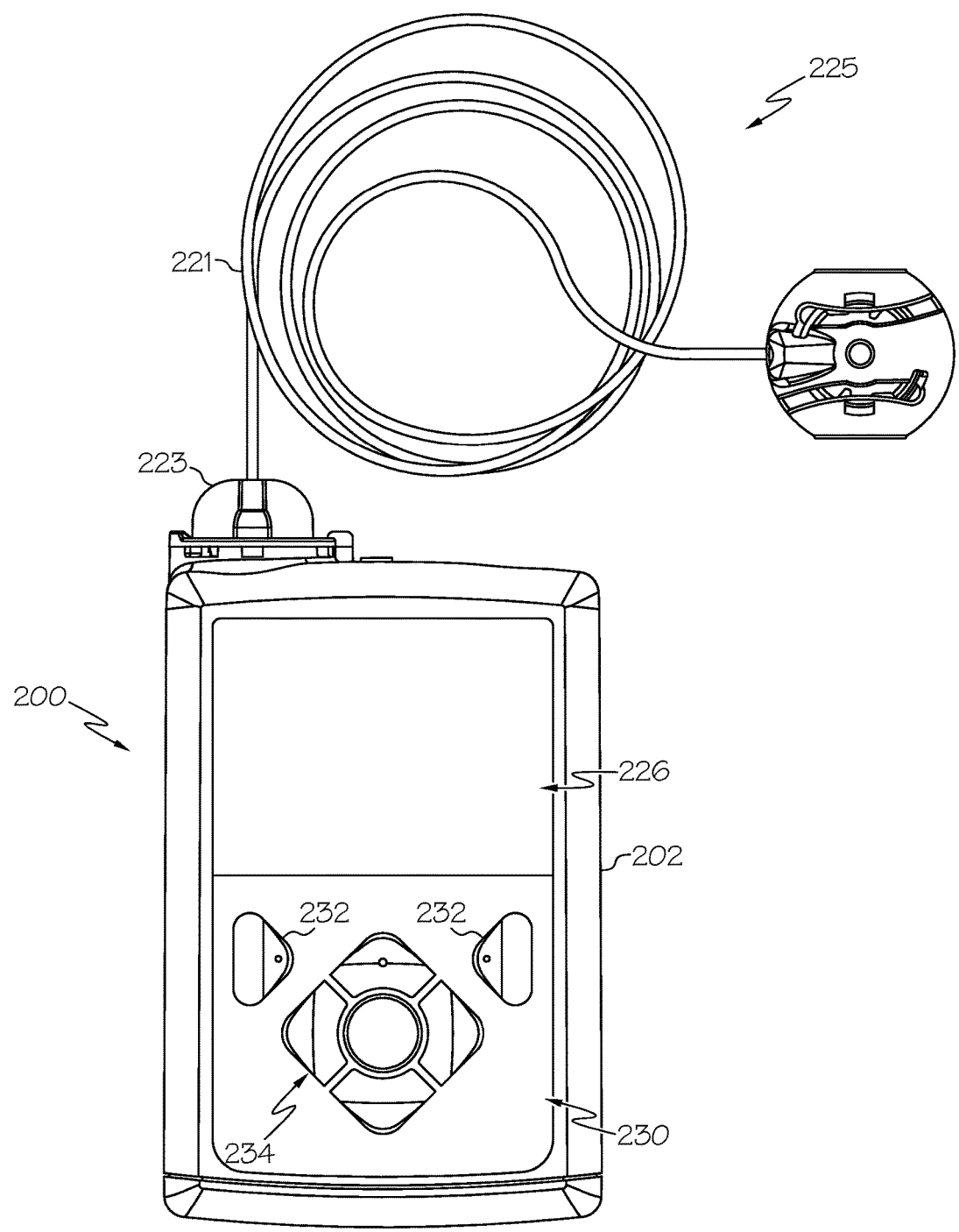
FIG. 2 depicts a plan view of an exemplary embodiment of a fluid infusion device suitable for use in the infusion system of FIG. 1.
Figure 3:
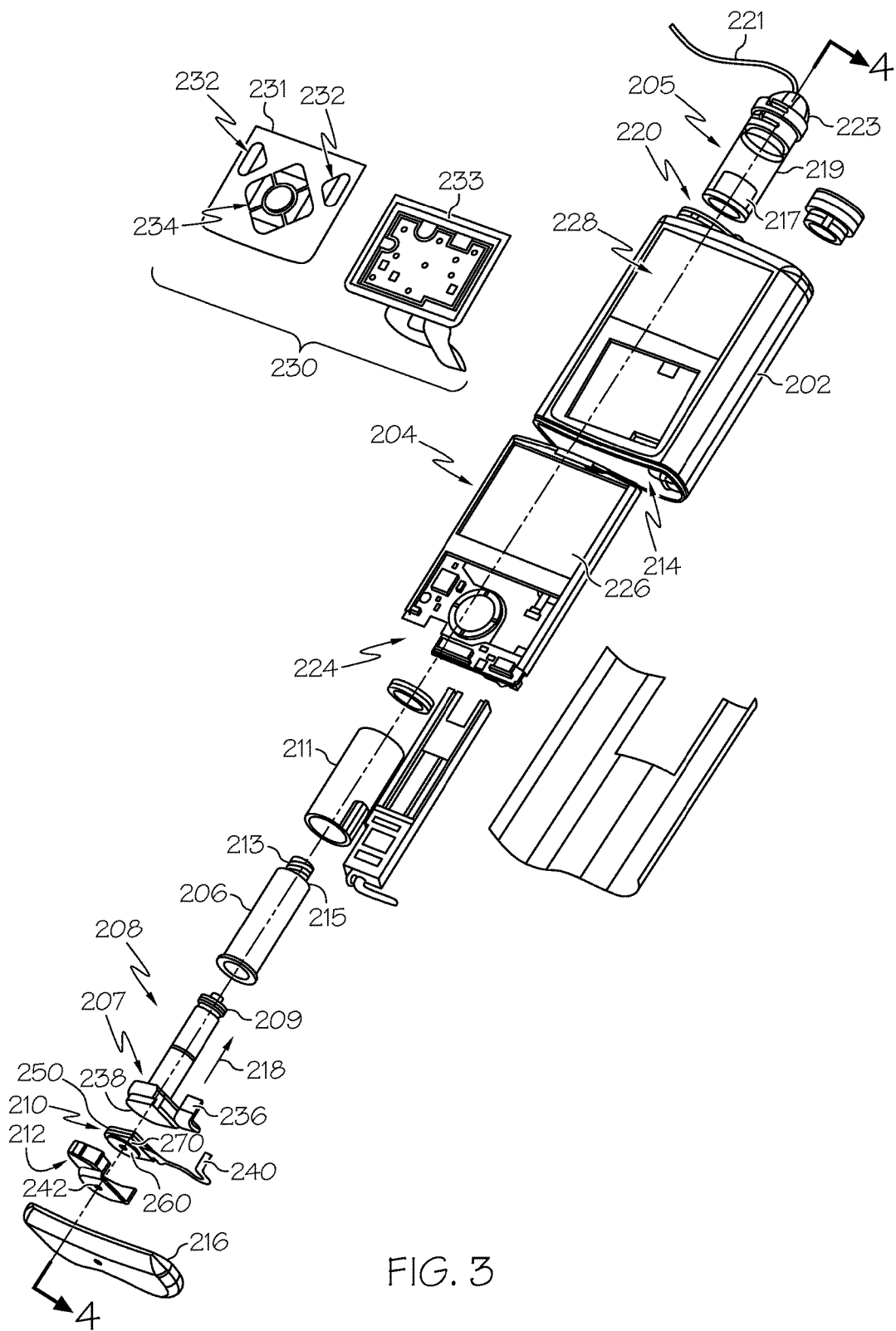
FIG. 3 is an exploded perspective view of the fluid infusion device of FIG. 2.
Figure 4:
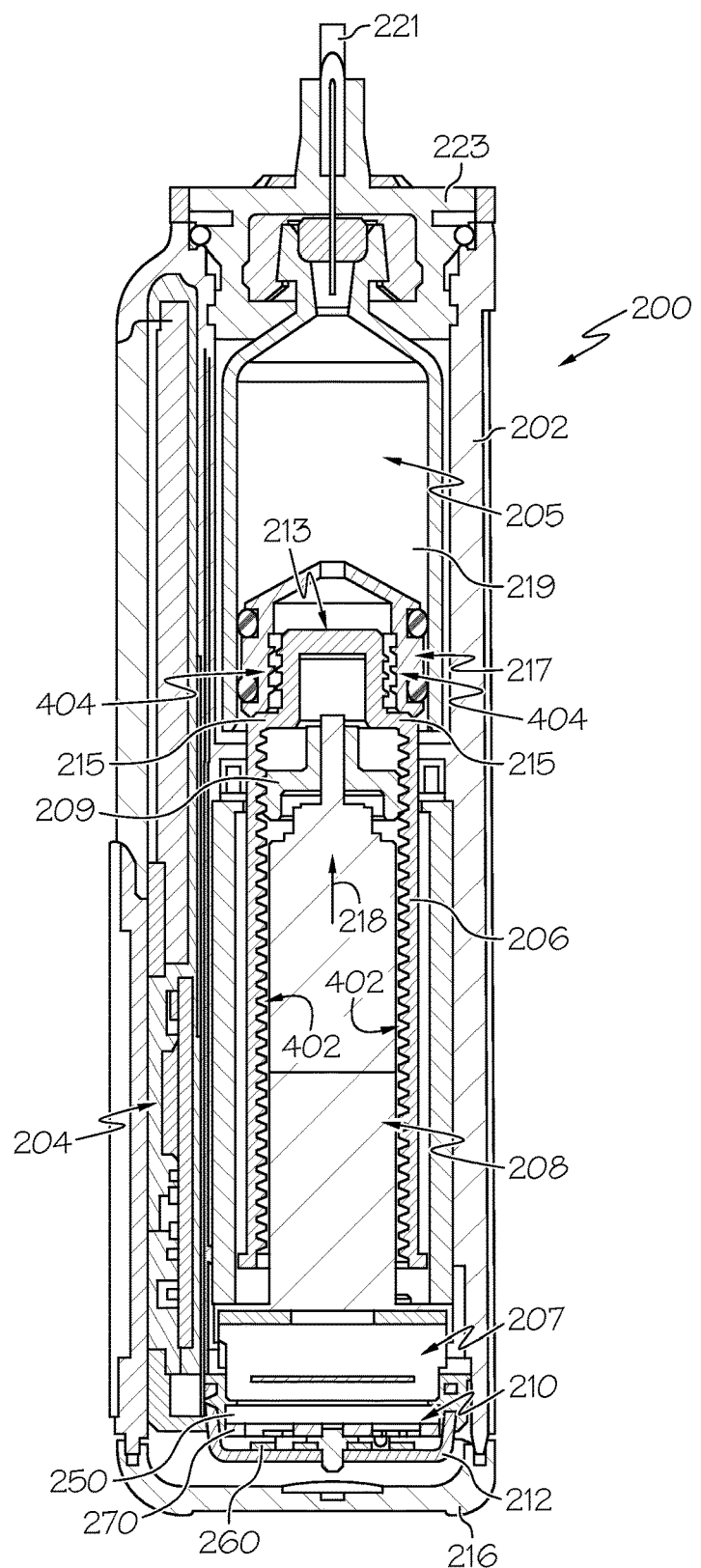
FIG. 4 is a cross-sectional view of the fluid infusion device of FIGS. 2-3 as viewed along line 4-4 in FIG. 3 when assembled with a reservoir inserted in the infusion device.

FIGS. 2-4 depict one exemplary embodiment of a fluid infusion device 200 (or alternatively, infusion pump) suitable for use in an infusion system, such as, for example, as infusion device 102 in the infusion system 100 of FIG. 1. The fluid infusion device 200 is a portable medical device designed to be carried or worn by a patient (or user), and the fluid infusion device 200 may leverage any number of conventional features, components, elements, and characteristics of existing fluid infusion devices, such as, for example, some of the features, components, elements, and/or characteristics described in U.S. Pat. Nos. 6,485,465 and 7,621,893. It should be appreciated that FIGS. 2-4 depict some aspects of the infusion device 200 in a simplified manner; in practice, the infusion device 200 could include additional elements, features, or components that are not shown or described in detail herein.

As best illustrated in FIGS. 2-3, the illustrated embodiment of the fluid infusion device 200 includes a housing 202 adapted to receive a fluid-containing reservoir 205. An opening 220 in the housing 202 accommodates a fitting 223 (or cap) for the reservoir 205, with the fitting 223 being configured to mate or otherwise interface with tubing 221 of an infusion set 225 that provides a fluid path to/from the body of the user. In this manner, fluid communication from the interior of the reservoir 205 to the user is established via the tubing 221. The illustrated fluid infusion device 200 includes a human-machine interface (HMI) 230 (or user interface) that includes elements 232, 234 that can be manipulated by the user to administer a bolus of fluid (e.g., insulin), to change therapy settings, to change user preferences, to select display features, and the like. The infusion device also includes a display element 226, such as a liquid crystal display (LCD) or another suitable display element, that can be used to present various types of information or data to the user, such as, without limitation: the current glucose level of the patient; the time; a graph or chart of the patient's glucose level versus time; device status indicators; etc.

The housing 202 is formed from a substantially rigid material having a hollow interior 214 adapted to allow an electronics assembly 204, a sliding member (or slide) 206, a drive system 208, a sensor assembly 210, and a drive system capping member 212 to be disposed therein in addition to the reservoir 205, with the contents of the housing 202 being enclosed by a housing capping member 216. The opening 220, the slide 206, and the drive system 208 are coaxially aligned in an axial direction (indicated by arrow 218), whereby the drive system 208 facilitates linear displacement of the slide 206 in the axial direction 218 to dispense fluid from the reservoir 205 (after the reservoir 205 has been inserted into opening 220), with the sensor assembly 210 being configured to measure axial forces (e.g., forces aligned with the axial direction 218) exerted on the sensor assembly 210 responsive to operating the drive system 208 to displace the slide 206. In various embodiments, the sensor assembly 210 may be utilized to detect one or more of the following: an occlusion in a fluid path that slows, prevents, or otherwise degrades fluid delivery from the reservoir 205 to a patient's body; when the reservoir 205 is empty; when the slide 206 is properly seated with the reservoir 205; when a fluid dose has been delivered; when the infusion pump 200 is subjected to shock or vibration; when the infusion pump 200 requires maintenance.

Depending on the embodiment, the fluid-containing reservoir 205 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. As best illustrated in FIGS. 3-4, the reservoir 205 typically includes a reservoir barrel 219 that contains the fluid and is concentrically and/or coaxially aligned with the slide 206 (e.g., in the axial direction 218) when the reservoir 205 is inserted into the infusion pump 200. The end of the reservoir 205 proximate the opening 220 may include or otherwise mate with the fitting 223, which secures the reservoir 205 in the housing 202 and prevents displacement of the reservoir 205 in the axial direction 218 with respect to the housing 202 after the reservoir 205 is inserted into the housing 202. As described above, the fitting 223 extends from (or through) the opening 220 of the housing 202 and mates with tubing 221 to establish fluid communication from the interior of the reservoir 205 (e.g., reservoir barrel 219) to the user via the tubing 221 and infusion set 225. The opposing end of the reservoir 205 proximate the slide 206 includes a plunger 217 (or stopper) positioned to push fluid from inside the barrel 219 of the reservoir 205 along a fluid path through tubing 221 to a user. The slide 206 is configured to mechanically couple or otherwise engage with the plunger 217, thereby becoming seated with the plunger 217 and/or reservoir 205. Fluid is forced from the reservoir 205 via tubing 221 as the drive system 208 is operated to displace the slide 206 in the axial direction 218 toward the opening 220 in the housing 202.

In the illustrated embodiment of FIGS. 3-4, the drive system 208 includes a motor assembly 207 and a drive screw 209. The motor assembly 207 includes a motor that is coupled to drive train components of the drive system 208 that are configured to convert rotational motor motion to a translational displacement of the slide 206 in the axial direction 218, and thereby engaging and displacing the plunger 217 of the reservoir 205 in the axial direction 218. In some embodiments, the motor assembly 207 may also be powered to translate the slide 206 in the opposing direction (e.g., the direction opposite direction 218) to retract and/or detach from the reservoir 205 to allow the reservoir 205 to be replaced. In exemplary embodiments, the motor assembly 207 includes a brushless DC (BLDC) motor having one or more permanent magnets mounted, affixed, or otherwise disposed on its rotor. However, the subject matter described herein is not necessarily limited to use with BLDC motors, and in alternative embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 205.

As best shown in FIG. 4, the drive screw 209 mates with threads 402 internal to the slide 206. When the motor assembly 207 is powered and operated, the drive screw 209 rotates, and the slide 206 is forced to translate in the axial direction 218. In an exemplary embodiment, the infusion pump 200 includes a sleeve 211 to prevent the slide 206 from rotating when the drive screw 209 of the drive system 208 rotates. Thus, rotation of the drive screw 209 causes the slide 206 to extend or retract relative to the drive motor assembly 207. When the fluid infusion device is assembled and operational, the slide 206 contacts the plunger 217 to engage the reservoir 205 and control delivery of fluid from the infusion pump 200. In an exemplary embodiment, the shoulder portion 215 of the slide 206 contacts or otherwise engages the plunger 217 to displace the plunger 217 in the axial direction 218. In alternative embodiments, the slide 206 may include a threaded tip 213 capable of being detachably engaged with internal threads 404 on the plunger 217 of the reservoir 205, as described in detail in U.S. Pat. Nos. 6,248,093 and 6,485,465, which are incorporated by reference herein.

As illustrated in FIG. 3, the electronics assembly 204 includes control electronics 224 coupled to the display element 226, with the housing 202 including a transparent window portion 228 that is aligned with the display element 226 to allow the display 226 to be viewed by the user when the electronics assembly 204 is disposed within the interior 214 of the housing 202. The control electronics 224 generally represent the hardware, firmware, processing logic and/or software (or combinations thereof) configured to control operation of the motor assembly 207 and/or drive system 208, as described in greater detail below in the context of FIG. 5. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 224 includes one or more programmable controllers that may be programmed to control operation of the infusion pump 200.

The motor assembly 207 includes one or more electrical leads 236 adapted to be electrically coupled to the electronics assembly 204 to establish communication between the control electronics 224 and the motor assembly 207. In response to command signals from the control electronics 224 that operate a motor driver (e.g., a power converter) to regulate the amount of power supplied to the motor from a power supply, the motor actuates the drive train components of the drive system 208 to displace the slide 206 in the axial direction 218 to force fluid from the reservoir 205 along a fluid path (including tubing 221 and an infusion set), thereby administering doses of the fluid contained in the reservoir 205 into the patient's body. Preferably, the power supply is realized one or more batteries contained within the housing 202. Alternatively, the power supply may be a solar panel, capacitor, AC or DC power supplied through a power cord, or the like. In some embodiments, the control electronics 224 may operate the motor of the motor assembly 207 and/or drive system 208 in a stepwise manner, typically on an intermittent basis; to administer discrete precise doses of the fluid to the user according to programmed delivery profiles.

Referring to FIGS. 2-4, as described above, the user interface 230 includes HMI elements, such as buttons 232 and a directional pad 234, that are formed on a graphic keypad overlay 231 that overlies a keypad assembly 233, which includes features corresponding to the buttons 232, directional pad 234 or other user interface items indicated by the graphic keypad overlay 231. When assembled, the keypad assembly 233 is coupled to the control electronics 224, thereby allowing the HMI elements 232, 234 to be manipulated by the user to interact with the control electronics 224 and control operation of the infusion pump 200, for example, to administer a bolus of insulin, to change therapy settings, to change user preferences, to select display features, to set or disable alarms and reminders, and the like. In this regard, the control electronics 224 maintains and/or provides information to the display 226 regarding program parameters, delivery profiles, pump operation, alarms, warnings, statuses, or the like, which may be adjusted using the HMI elements 232, 234. In various embodiments, the HMI elements 232, 234 may be realized as physical objects (e.g., buttons, knobs, joysticks, and the like) or virtual objects (e.g., using touch-sensing and/or proximity-sensing technologies). For example, in some embodiments, the display 226 may be realized as a touch screen or touch-sensitive display, and in such embodiments, the features and/or functionality of the HMI elements 232, 234 may be integrated into the display 226 and the HMI 230 may not be present. In some embodiments, the electronics assembly 204 may also include alert generating elements coupled to the control electronics 224 and suitably configured to generate one or more types of feedback, such as, without limitation: audible feedback; visual feedback; haptic (physical) feedback; or the like.

Referring to FIGS. 3-4, in accordance with one or more embodiments, the sensor assembly 210 includes a back plate structure 250 and a loading element 260. The loading element 260 is disposed between the capping member 212 and a beam structure 270 that includes one or more beams having sensing elements disposed thereon that are influenced by compressive force applied to the sensor assembly 210 that deflects the one or more beams, as described in greater detail in U.S. Pat. No. 8,474,332, which is incorporated by reference herein. In exemplary embodiments, the back plate structure 250 is affixed, adhered, mounted, or otherwise mechanically coupled to the bottom surface 238 of the drive system 208 such that the back plate structure 250 resides between the bottom surface 238 of the drive system 208 and the housing cap 216. The drive system capping member 212 is contoured to accommodate and conform to the bottom of the sensor assembly 210 and the drive system 208. The drive system capping member 212 may be affixed to the interior of the housing 202 to prevent displacement of the sensor assembly 210 in the direction opposite the direction of force provided by the drive system 208 (e.g., the direction opposite direction 218). Thus, the sensor assembly 210 is positioned between the motor assembly 207 and secured by the capping member 212, which prevents displacement of the sensor assembly 210 in a downward direction opposite the direction of arrow 218, such that the sensor assembly 210 is subjected to a reactionary compressive force when the drive system 208 and/or motor assembly 207 is operated to displace the slide 206 in the axial direction 218 in opposition to the fluid pressure in the reservoir 205. Under normal operating conditions, the compressive force applied to the sensor assembly 210 is correlated with the fluid pressure in the reservoir 205. As shown, electrical leads 240 are adapted to electrically couple the sensing elements of the sensor assembly 210 to the electronics assembly 204 to establish communication to the control electronics 224, wherein the control electronics 224 are configured to measure, receive, or otherwise obtain electrical signals from the sensing elements of the sensor assembly 210 that are indicative of the force applied by the drive system 208 in the axial direction 218.

Figure 5:
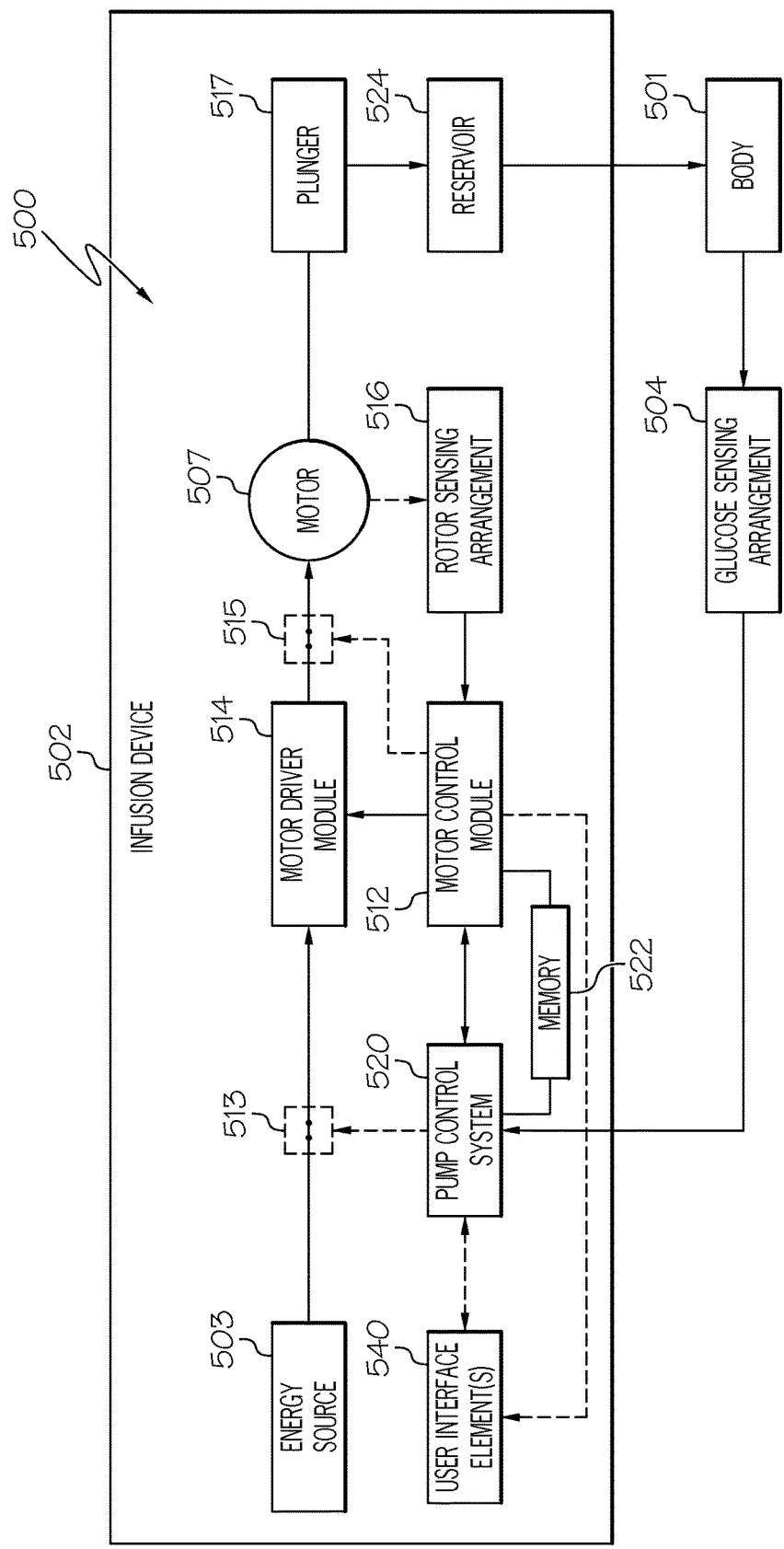
FIG. 5 is a block diagram of an exemplary control system suitable for use in a fluid infusion device, such as the fluid infusion device of FIG. 1 or FIG. 2.

FIG. 5 depicts an exemplary embodiment of a control system 500 suitable for use with an infusion device 502, such as the infusion device 102 in FIG. 1 or the infusion device 200 of FIG. 2. The control system 500 is configured to control or otherwise regulate a physiological condition in the body 501 of a patient (or user). In one or more exemplary embodiments, the condition being regulated is sensed, detected, measured or otherwise quantified by a sensing arrangement 504 (e.g., sensing arrangement 104) communicatively coupled to the infusion device 502. However, it should be noted that in alternative embodiments, the condition being regulated by the control system 500 may be correlative to the measured values obtained by the sensing arrangement 504. That said, for clarity and purposes of explanation, the subject matter may be described herein in the context of the sensing arrangement 504 being realized as a glucose sensing arrangement that senses, detects, measures or otherwise quantifies the user's glucose level, which is being regulated in the body 501 of the user by the control system 500.

In exemplary embodiments, the sensing arrangement 504 includes one or more interstitial glucose sensing elements that generate or otherwise output electrical signals having a signal characteristic that is correlative to, influenced by, or otherwise indicative of the relative interstitial fluid glucose level in the body 501 of the user. The output electrical signals are filtered or otherwise processed to obtain a measurement value indicative of the user's interstitial fluid glucose level. A blood glucose meter, such as a finger stick device, may be utilized to directly sense, detect, measure or otherwise quantify the blood glucose in the body 501 of the user and output or otherwise provide a measured blood glucose value that may be utilized as a reference measurement for calibrating the sensing arrangement 504, and thereby converting a measurement value indicative of the user's interstitial fluid glucose level into a corresponding calibrated blood glucose measurement value. For purposes of explanation, sensor glucose value, sensed glucose value, glucose measurement value, or variants thereof should be understood to encompass any glucose value indicative of a current measured glucose level in the body of the user that is based on the electrical signals output by the sensing element(s) of the sensing arrangement 504.

The pump control module 520 generally represents the electronics and other components of the infusion device 502 that control operation of the fluid infusion device 502 according to a desired infusion delivery program in a manner that may be influenced by the sensed glucose value indicative of a current glucose level in the body 501 of the user. The particular operating mode being implemented by the pump control module 520 influences the generated dosage commands for operating the motor 507 to displace the plunger 517 within a fluid reservoir 524 and deliver insulin to the body 501 of the user. For example, in a closed-loop (CL) operating mode, the pump control module 520 generates or otherwise determines dosage commands for operating the motor 507 based on the difference between a sensed glucose value and the target (or commanded) glucose value to regulate the sensed glucose value to the target value. In other operating modes, the pump control module 520 may generate or otherwise determine dosage commands configured to maintain the sensed glucose value below an upper glucose limit, above a lower glucose limit, or otherwise within a desired range of glucose values. In practice, the infusion device 502 may store or otherwise maintain the target glucose value and/or other glucose control value(s) in a data storage element (or memory) 522 accessible to the pump control module 520.

The target glucose value and other threshold values may be received from an external component (e.g., CCD 106 and/or computing device 108) or be input by a user via a user interface element 540 associated with the infusion device 502. In practice, the one or more user interface element(s) 540 associated with the infusion device 502 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 540 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the user. It should be noted that although FIG. 5 depicts the user interface element(s) 540 as being integrated with the infusion device 502, in practice, one or more of the user interface element(s) 540 may be separate from the infusion device 502. The user interface element(s) 540 may be manipulated by the user to operate the infusion device 502 to deliver correction boluses, adjust target and/or threshold values, modify the delivery control scheme or operating mode, and the like, as desired.

Additionally, output user interface element(s) 540 may be utilized by the pump control module 520 or the motor control module 512 to generate alerts or other user notifications in response to anomalous conditions encountered during operation of the infusion device 502, as described in greater detail below. In some embodiments, the control modules 512, 520 are coupled to different output user interface elements 540 from one another, so that the motor control module 512 utilizes a first set of one or more output user interface elements 540 to generate alerts while the pump control module 520 utilizes a different set of one or more output user interface elements 540 to generate alerts. For example, the motor control module 512 may provide user notifications via a light-emitting diode (LED) element and/or a haptic feedback element (e.g., a vibrating element), with the pump control module 520 providing user notifications via an auditory output element (e.g., a piezoelectric audio transducer) and/or a LCD display (e.g., display element 226).

Depending on the embodiment, the pump control module 520 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. The motor control module 512 is separate from the pump control module 520, and may similarly be implemented or realized with a general purpose processor, a microprocessor, a controller, a microcontroller, a state machine, an application specific integrated circuit, or the like. The control modules 512, 520 are communicatively coupled to one another via a communications bus or similar communications interface to support the processes described herein.

Still referring to FIG. 5, the motor control module 512 is coupled to the motor 507 (e.g., motor assembly 207) of the infusion device 502 via a motor driver module 514 coupled between an energy source 503 and the motor 507. The motor 507 is operable to displace a plunger 517 (e.g., plunger 217 via drive system 208) in a reservoir 524 (e.g., reservoir 205) and provide a desired amount of fluid to the body 501 of a user. In this regard, displacement of the plunger 517 results in the delivery of a fluid that is capable of influencing the condition in the body 501 of the user to the body 501 of the user via a fluid delivery path (e.g., via tubing 221 of an infusion set 225). The motor control module 512 is coupled to the motor driver module 514, and the motor control module 512 generates or otherwise provides command signals that operate the motor driver module 514 to provide power (or current) from the energy source 503 to the motor 507 to displace the plunger 517 in response to receiving, from the pump control module 520, a dosage command indicative of the desired amount of fluid to be delivered.

In exemplary embodiments, the energy source 503 is realized as a battery housed within the infusion device 502 (e.g., within housing 202) that provides direct current (DC) power. In this regard, the motor driver module 514 generally represents the combination of circuitry, hardware and/or other electrical components configured to convert or otherwise transfer DC power provided by the energy source 503 into alternating electrical signals applied to respective phases of the stator windings of the motor 507 that result in current flowing through the stator windings that generates a stator magnetic field and causes the rotor of the motor 507 to rotate.

The motor control module 512 is configured to receive or otherwise obtain a commanded dosage from the pump control module 520, convert the commanded dosage to a commanded translational displacement of the plunger 517, and command, signal, or otherwise operate the motor driver module 514 to cause the rotor of the motor 507 to rotate by an amount that produces the commanded translational displacement of the plunger 517. For example, the motor control module 512 may determine an amount of rotation of the rotor required to produce translational displacement of the plunger 517 that achieves the commanded dosage received from the pump control module 520. Based on the current rotational position (or orientation) of the rotor with respect to the stator that is indicated by the output of the rotor sensing arrangement 516, the motor control module 512 determines the appropriate sequence of alternating electrical signals to be applied to the respective phases of the stator windings that should rotate the rotor by the determined amount of rotation from its current position (or orientation). In embodiments where the motor 507 is realized as a BLDC motor, the alternating electrical signals commutated the respective phases of the stator windings at the appropriate orientation of the rotor magnetic poles with respect to the stator and in the appropriate order to provide a rotating stator magnetic field that rotates the rotor in the desired direction. Thereafter, the motor control module 512 operates the motor driver module 514 to apply the determined alternating electrical signals (e.g., the command signals) to the stator windings of the motor 507 to achieve the desired delivery of fluid to the user.

In exemplary embodiments described herein, electrical power output from the energy source 503 is selectively provided to the input of the motor driver module 514 under control of the pump control module 520. For example, a switching arrangement 513 may be provided effectively electrically in series between the output of the energy source 503 (or a bus connected to the energy source 503) and the input to the motor driver module 514. In exemplary embodiments, the pump control module 520 operates the switching arrangement 513 to electrically disconnect the motor driver module 514 from the electrical power output by the energy source 503 (e.g., by opening or deactivating one or more switches) when the motor 507 is not being utilized to deliver fluid to the body 501 of the user. When the pump control module 520 determines it is desirable to operate the motor 507 to implement a dosage command, the pump control module 520 operates the switching arrangement 513 to electrically connect the energy source 503 and the motor driver module 514 to enable input electrical power to the motor driver module 514 from the energy source 503 in accordance with a handshaking sequence of communications with the motor control module 512. As described in greater detail below, in response to identifying or otherwise detecting an anomalous condition with respect to the pump control module 520, the pump control module 520 automatically operates the switching arrangement 513 to electrically disconnect the energy source 503 from the motor driver module 514 to disable or otherwise remove input power to the motor 507 and/or motor driver module 514.

Still referring to FIG. 5, in exemplary embodiments described herein, electrical power output from the motor driver module 514 is selectively provided to the input(s) of the motor 507 under control of the motor control module 512. For example, a second switching arrangement 515 may be provided effectively electrically in series between the output of the motor driver module 514 and the input(s) (e.g., the stator winding(s)) of the motor 507. Thus, the motor control module 512 may operate the switching arrangement 515 to electrically disconnect the motor 507 from the output of the motor driver module 514, thereby preventing power from being applied to the motor 507. In this regard, the switching arrangement 515 provides redundancy for disconnecting the motor 507 from the electrical power from the energy source 503. Prior to operating the motor driver module 514 to implement a dosage command, the motor control module 512 operates the switching arrangement 515 to electrically connect the output of the motor driver module 514 to the motor 507 to enable electrical power being applied to the motor 507 in accordance with a second handshaking sequence of communications with the pump control module 520. In response to identifying or otherwise detecting an anomalous condition with respect to the motor control module 512, the motor control module 512 automatically operates the switching arrangement 515 to electrically disconnect the motor 507 from the motor driver module 514 to disable or otherwise remove input power to the motor 507, as described in greater detail below.

It should be appreciated that FIG. 5 is a simplified representation of the infusion device 502 for purposes of explanation and is not intended to limit the subject matter described herein in any way. In this regard, depending on the embodiment, the features and/or functionality of the switching arrangement 513 may be implemented by or otherwise integrated into the energy source 503 or the motor driver module 514. Similarly, the features and/or functionality of the switching arrangement 515 may be implemented by or otherwise integrated into the motor driver module 514 or the motor 507. Thus, while the subject matter is described herein in the context of discrete switching arrangements 513, 515 that enable or otherwise provide a path for input power to the motor 507 from the energy source 503, in practice, discrete switching arrangements 513, 515 may not be present in an embodiment of the infusion device 502. For example, the functionality of the switching arrangements 513, 515 may be integrated into a motor driver module 514 which includes enable/disable functionality associated with its input and output, in which case, the pump control module 520 will be coupled to the motor driver module 514 to control the status (e.g., enabled or disabled) of the input power to the motor driver module 514, while the motor control module 512 coupled to the motor driver module 514 to control the status (e.g., enabled or disabled) of the output power from the motor driver module 514.

Figure 6:
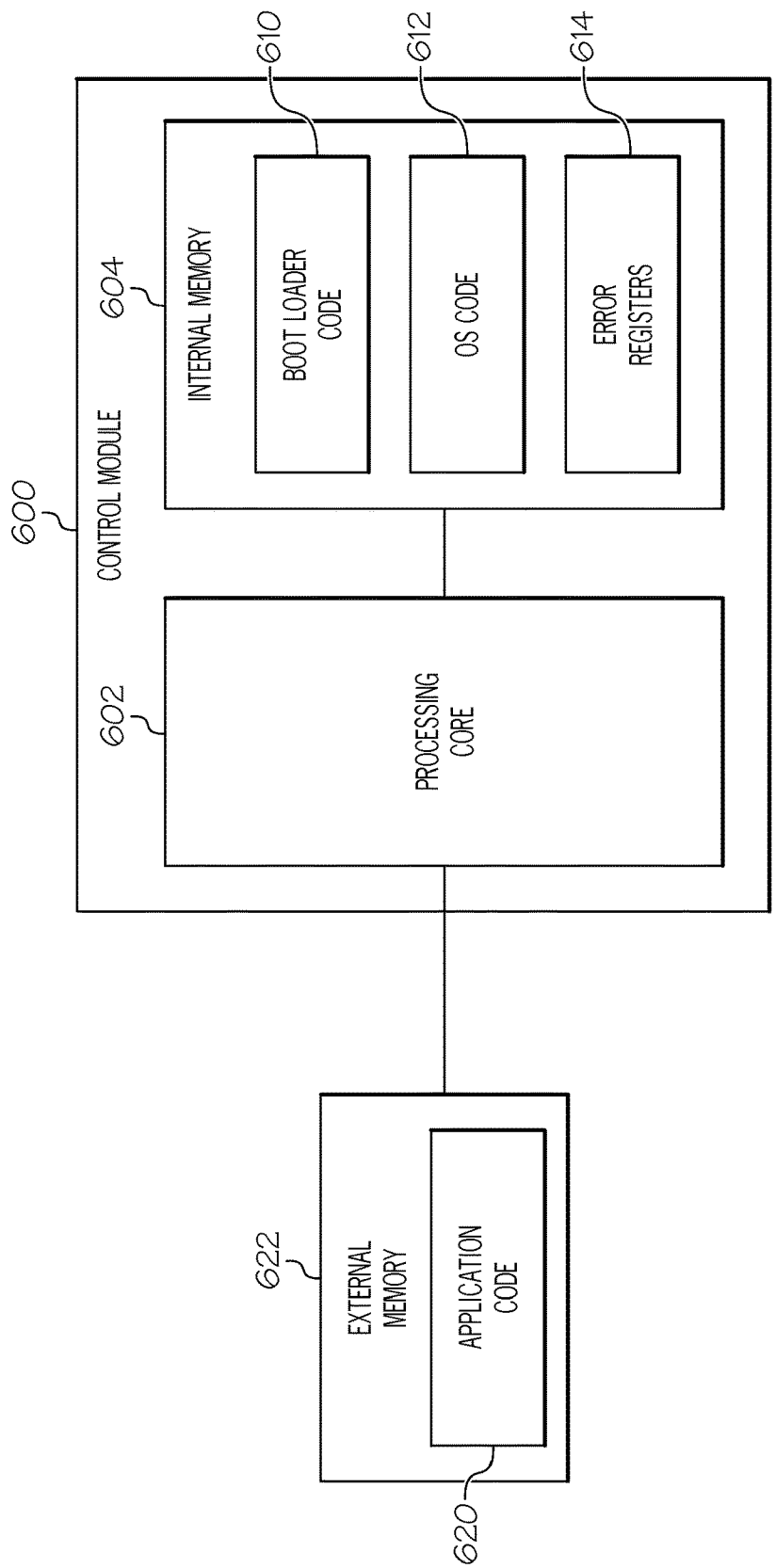
FIG. 6 is a block diagram of an exemplary control module suitable for use in the control system of FIG. 5.

FIG. 6 depicts an exemplary embodiment of a control module 600 suitable for use as the pump control module 520 or the motor control module 512 in the infusion device 502 of FIG. 5. For example, the pump control module 520 may be realized as a first instance of the control module 600 that executes or otherwise implements a delivery control application that supports closed-loop generation of dosage commands based on a glucose measurement value from the sensing arrangement 504 as described above, while the motor control module 512 is realized as a second instance of the control module 600 that executes or otherwise implements a motor control application that converts received dosage commands into corresponding motor control commands and supports operating the motor driver module 514 to deliver input power corresponding to those motor control commands to the motor 507 and achieve the commanded dosage of insulin. It should be understood that FIG. 6 is a simplified representation of a control module 600 for purposes of explanation and is not intended to limit the subject matter described herein in any way.

The control module 600 includes a processing core 602 that includes, accesses, or is otherwise coupled to a data storage arrangement 604. In exemplary embodiments, the data storage arrangement 604 is integrated with the processing core 602 in a common device package to provide the control module 600. In this regard, the data storage arrangement 604 represents the registers, caches, and/or other non-transitory non-volatile data storage media at the higher levels of the memory hierarchy which are typically internal to or otherwise integrated with the control module 600. Accordingly, for purposes of explanation, but without limitation, the data storage arrangement 604 may alternatively be referred to herein as internal memory 604 of the control module 600.

The processing core 602 generally represents the combination of hardware, circuitry, logic, and/or the like that is configured to retrieve and execute instructions and perform the tasks, operations, functions and/or processes specified by the instructions. In this regard, the processing core 602 may include one or more instruction fetching arrangements, instructing decoding arrangements, arithmetic logic unit(s) (ALUs) and/or other execution arrangements, memory access arrangements, and the like, and the processing core 602 may be configured to support instruction parallelization, depending on the needs of a particular embodiment.

The internal memory 604 includes computer-executable programming instructions that are read and executed by the processing core 602 to support or otherwise perform one or more of the various tasks, operations, functions, and/or processes described herein. In exemplary embodiments, the internal memory 604 persistently stores or otherwise maintains boot loader program code 610, which is read and executed by the processing core 602 upon initialization or reset of the control module 600 to perform various power-on self-tests and other diagnostic checks described herein. Additionally, the internal memory 604 stores or otherwise maintains operating system program code 612, which is loaded by the boot loader and then read and executed by the processing core 602 to manage or otherwise support interactions with other components of the infusion device 502. In this regard, the operating system executed by the processing core 602 facilitates or otherwise supports the processing core 602 accessing another data storage element 622 external to the control module 600 (e.g., memory 522) to retrieve or otherwise obtain application code 620, which, in turn, is utilized by the control module 600 to interact with or otherwise control another component of the infusion device 502.

In exemplary embodiments, operating system executing on the control module 600 detects or otherwise identifies anomalous conditions with respect to the control module 600 during execution of the application code 620, as described in greater detail below. In this regard, the internal memory 604 includes a dedicated portion 614 for storing or otherwise maintaining diagnostic information for anomalous conditions detected or otherwise identified by the operating system. For purposes of explanation, the allocated portion 614 that stores diagnostic information for anomalous conditions is alternatively referred to herein as the error registers. In exemplary embodiments, the error registers 614 are capable of storing diagnostic information for a finite number of anomalous conditions, which corresponds to the reset limit of the control module 600, as described in greater detail below.

Figure 7:
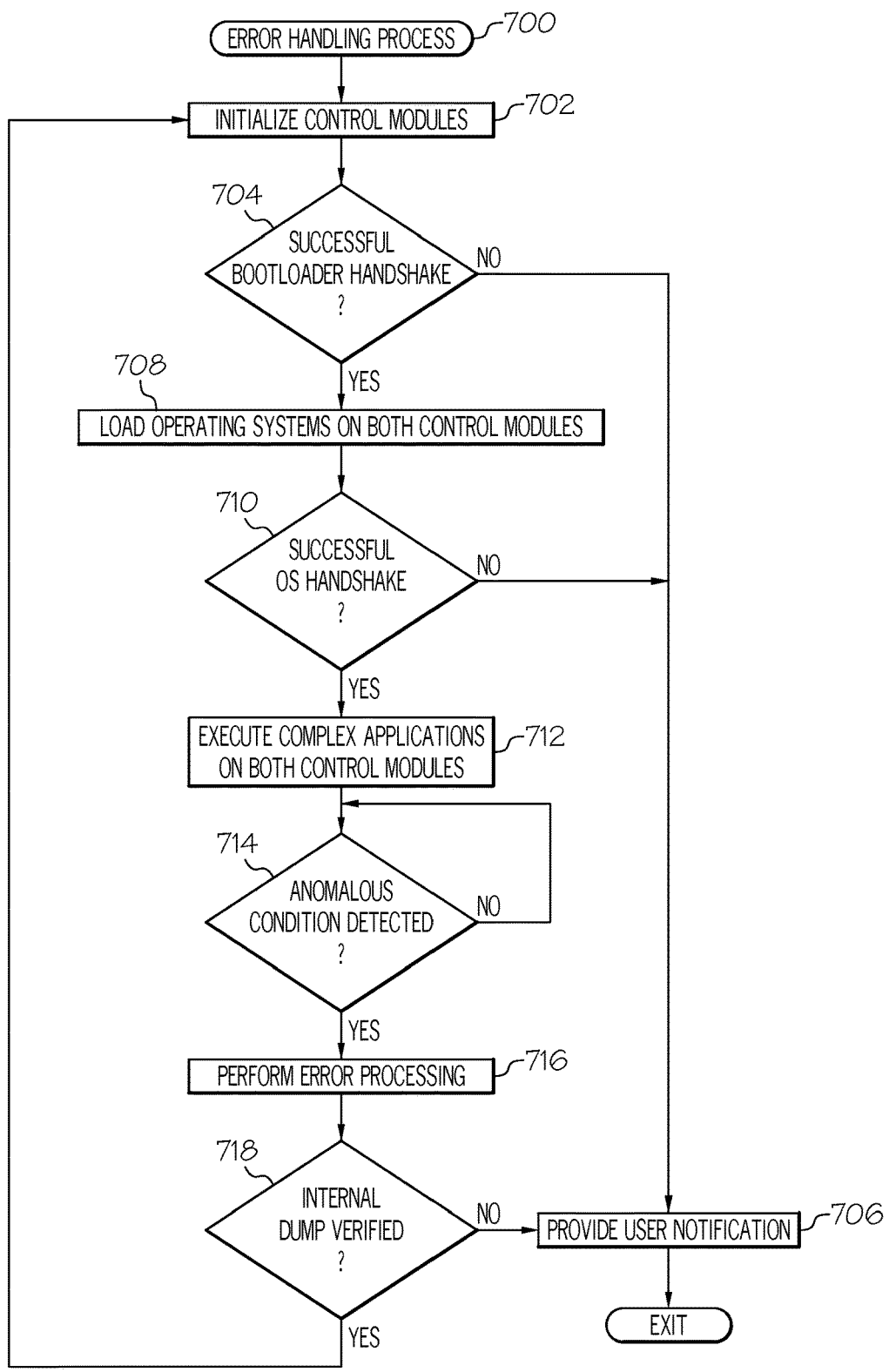
FIG. 7 is a flow diagram of an exemplary error handling process suitable for use with the control system of FIG. 5 in accordance with one or more embodiments.

FIG. 7 depicts an exemplary error handling process 700 suitable for implementation by the control modules 512, 520 of a control system 500 associated with an infusion device 502 to safely operate the motor 507 and recover from errors or other anomalous conditions detected during operation. For purposes of explanation, the error handling process 700 may be described herein in the context of a closed-loop operating mode, however, it will be appreciated that the subject matter described herein is not limited to the particular operating mode being implemented. Various tasks performed in connection with the error handling process 700 may be performed by hardware, firmware, software executed by processing circuitry, or any combination thereof. For illustrative purposes, the following description refers to elements mentioned above in connection with FIGS. 1-6. In practice, portions of the error handling process 700 may be performed by different elements of the control system 500, such as, for example, the control modules 512, 520, 600, the processing core(s) 602, internal memory 604, external memory 522, 622, the switching arrangements 513, 515, the motor driver module 514, the rotor sensing arrangement 516 and/or the user interface element(s) 540. It should be appreciated that the error handling process 700 may include any number of additional or alternative tasks, the tasks need not be performed in the illustrated order and/or the tasks may be performed concurrently, and/or the error handling process 700 may be incorporated into a more comprehensive procedure or process having additional functionality not described in detail herein. Moreover, one or more of the tasks shown and described in the context of FIG. 7 could be omitted from a practical embodiment of the error handling process 700 as long as the intended overall functionality remains intact.

The error handling process 700 begins by initializing the control modules of the infusion device to a boot loader stage and verifying or otherwise confirming successful communications between the control modules (tasks 702, 704). In this regard, when the infusion device 502 is initially powered on, each of the processing cores 602 of the respective control modules 512, 520 automatically loads or otherwise executes the respective boot loader code 610 stored in its internal memory 604. As described in greater detail below in the context of FIGS. 8-9, the boot loader 610 of each of the infusion device control modules 512, 520 is configured to perform a handshake with the boot loader 610 of the other control module 512, 520 before loading its respective operating system code 612. The initial boot loader handshaking sequence of communications verifies or otherwise ensures that the infusion device control modules 512, 520 have both passed their initial self-tests and are initialized into a stable known state before proceeding towards execution of more complex applications.

In the absence of a successful handshake between boot loaders of the infusion device control modules, the error handling process 700 automatically generates or otherwise provides a user notification indicating an anomalous condition of the infusion device that requires attention (task 706).

In this regard, when a boot loader 610 of one control module 512, 520 fails to receive a handshaking communication from the boot loader 610 executing on the other control module 512, 520 within a prescribed timeout period of time, the boot loader 610 may automatically operate one or more output user interface elements 540 coupled to its respective control module 512, 520 to provide an auditory, visual and/or haptic output that indicates or otherwise notifies the user of a problem with the infusion device 502. In some embodiments, the control module 512, 520 may disable further operation of the infusion device 502 to deliver fluid to the patient, for example, by deactivating or otherwise disconnecting the energy source 503 from the motor 507 via its associated switching element 513, 515.

In response to a successful handshake between boot loaders, the error handling process 700 continues by loading or otherwise executing the operating systems on the infusion device control modules and verifying or otherwise confirming successful communications between the operating systems at the operating system loading stage prior to executing additional application code (tasks 708, 710). In this regard, the boot loader 610 of each infusion device control module 512, 520 is configured to load the operating system code 612 into the respective processing core 602 automatically in response to a successful handshaking sequence of communications with the boot loader 610 of the other control module 512, 520. Thereafter, the executing operating systems 612 are configured to automatically perform another handshaking sequence of communications to verify or otherwise ensure that the operating systems of both infusion device control modules 512, 520 have been loaded and are executing properly before proceeding with execution of more complex applications. In the absence of a successful handshake between operating systems of the infusion device control modules, the error handling process 700 automatically generates or otherwise provides a user notification indicating an anomalous condition of the infusion device that requires attention in a similar manner as described above (task 706).

In response to a successful handshake between operating systems, the error handling process 700 continues by loading or otherwise executing complex applications on the infusion device control modules to operate the infusion device and achieve a desired delivery of fluid to a patient as needed (task 712). In this regard, the operating system 612 of the pump control module 520 may automatically load complex application code 620 into the processing core 602, which, when read and executed by the processing core 602, supports the pump control module 520 receiving sensed glucose values from the sensing arrangement 504 and calculating or otherwise determining dosage commands (or delivery commands) for operating the motor 507 to deliver fluid to the patient. For example, the processing core 602 may execute closed-loop delivery control application code 620 that supports determining dosage commands based on a difference between a current sensed glucose value obtained via the sensing arrangement 504 and a target glucose value to regulate the glucose value in the patient's body 501 to the target glucose value. Similarly, the operating system 612 of the motor control module 512 may automatically load complex application code 620 into its processing core 602, which, when read and executed by the processing core 602, supports the motor control module 512 receiving dosage commands (or delivery commands) from the pump control module 520, converting the dosage commands into corresponding motor commands, and operating the motor driver module 514 to effectuate those motor commands and deliver the commanded dosage of fluid to the body 501 of the patient.

During operation of the infusion device, the error handling process 700 continually monitors the operational status of the control modules to detect or otherwise identify the presence of an anomalous condition or other erroneous state (task 714). In response to detecting an anomalous condition, the error handling process 700 performs one or more error processing operations to mitigate the anomalous condition and verifies or otherwise confirms that diagnostic information pertaining to the anomalous condition has been successfully stored or otherwise written to internal memory before reinitializing the control modules (tasks 716, 718).

In exemplary embodiments, the operating systems 612 on the control modules 512, 520 are configured to periodically perform handshaking communications or transmit heartbeat messages and/or acknowledgments to one another indicating normal operational status. The operating system 612 on a respective control module 512, 520 may thereby detect an anomalous condition in response to the absence of a communication from the operating system 612 of the other control module 512, 520 within a handshaking or heartbeat timeout period. Alternatively, the operating system 612 on a respective control module 512, 520 may detect an anomalous condition in response to the overlying application code 620 encountering an exception or other unexpected error that cannot be mitigated by exception handling or other features provided by the application code 620. In response to detecting an anomalous condition, the operating system 612 on the respective control module 512, 520 automatically signals or otherwise operates the switching arrangement 513, 515 associated with its control module 512, 520 to disconnect or otherwise disable input electrical power to the motor 507 from the energy source 503. The operating system 612 then stores or otherwise maintains diagnostic information indicative of the current execution state of the processing core 602 to one or more error registers 614, and verifies the diagnostic information was completely written to the error register(s) 614 before resetting or otherwise reinitializing the processing core 602 to execute the boot loader code 610 (e.g., a hard reset). In this regard, when the diagnostic information pertaining to the anomalous condition cannot be successfully written to internal memory, the error handling process 700 automatically generates or otherwise provides a user notification in a similar manner as described above (task 706).

As described in greater detail below, when one control module 512, 520 of the infusion device 502 detects an anomalous condition and resets itself by reinitializing its boot loader 610, the operating system 612 of the other control module 512, 520 may detect or otherwise identify an anomalous condition in response to the absence of a handshake with (or heartbeat from) the other control module 512, 520. In response, the other operating system 612 of the other control module 512, 520 automatically signals or otherwise operates its associated switching arrangement 513, 515 to disconnect input electrical power to the motor 507, stores the diagnostic information indicative of the current execution state of its own processing core 602 to its internal memory 604, 614, and verifies its diagnostic information successfully stored before resetting or otherwise reinitializing its processing core 602 to execute its boot loader code 610. In this manner, when both control modules 512, 520 are both able to reinitialize to their respective boot loaders 610, the error handling process 700 repeats up until the number of anomalous conditions has met a threshold number (e.g., the reset error limit), at which point at least one of the control modules 512, 520 will generate a user notification that indicates that the infusion device 502 requires maintenance or other manual attention.

Figure 8:
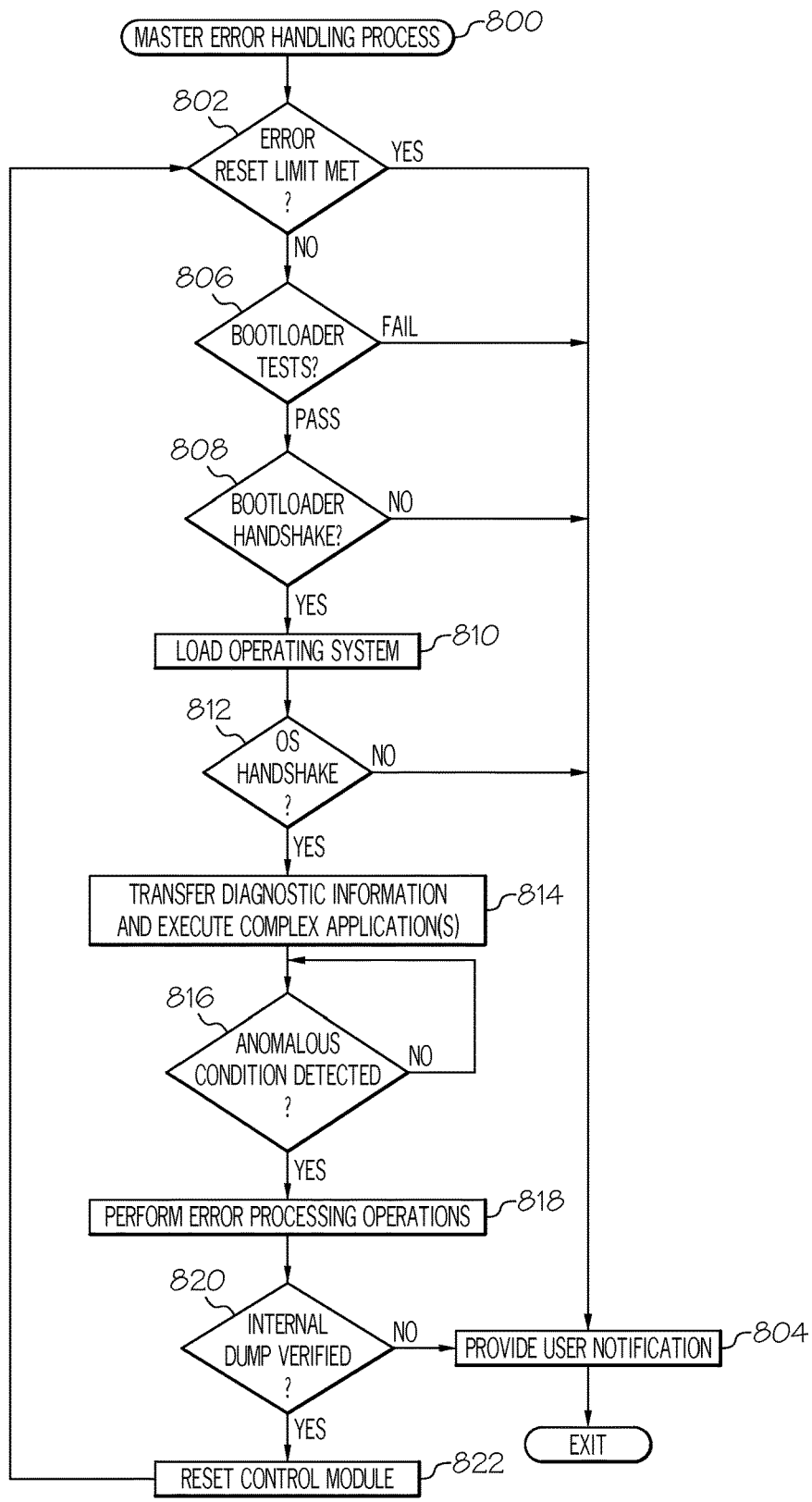
FIGS. 8-9 are flow diagram of exemplary error handling processes suitable for implementation by respective control modules in the control system of FIG. 5 in conjunction with the error handling process of FIG. 7 in accordance with one or more embodiments.
Figure 9:
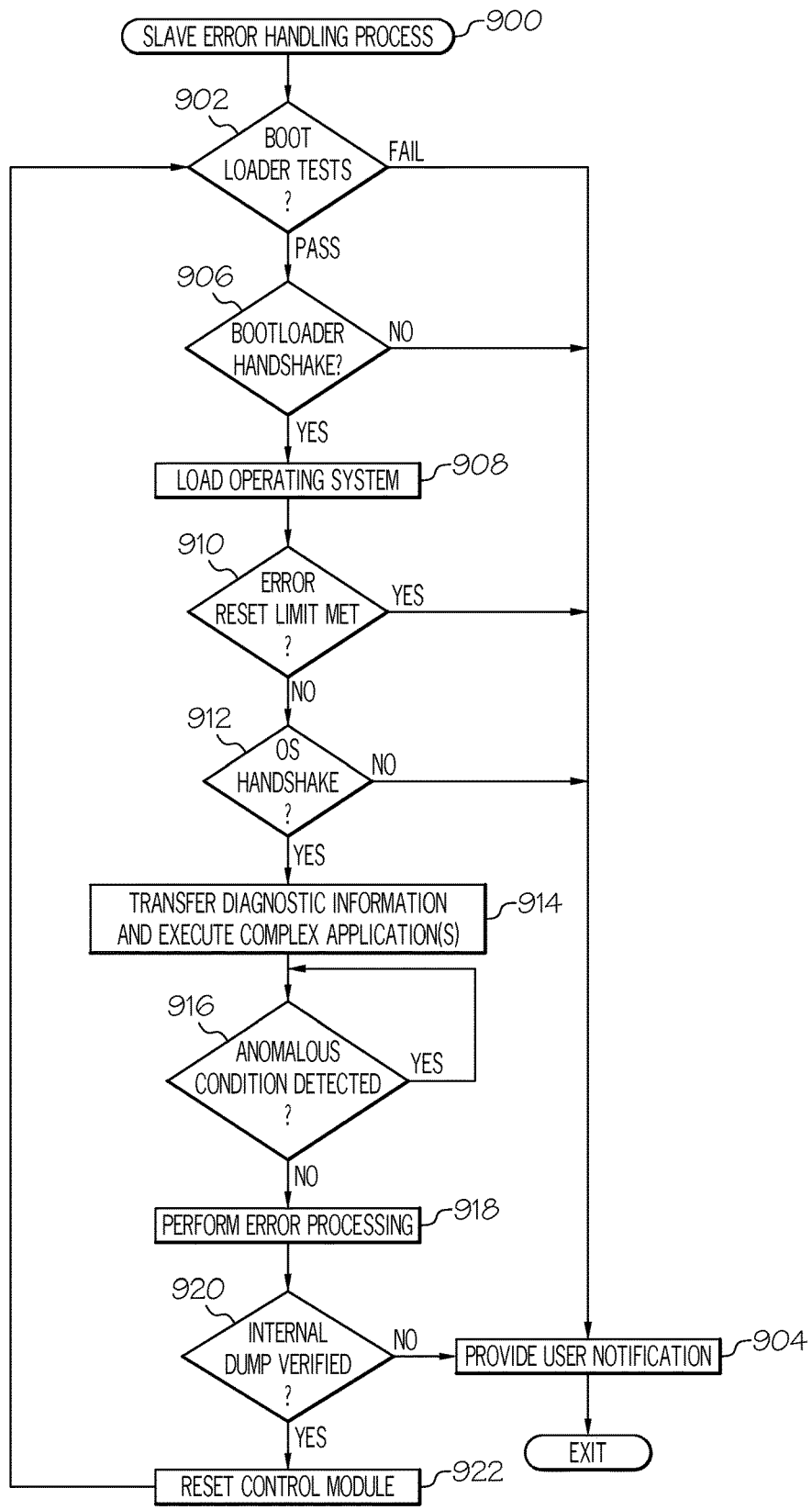

FIG. 8 depicts an exemplary error handling process 800 suitable for implementation by one of the control modules 512, 520 of the infusion device 502 in conjunction with the error handling process 700 of FIG. 7, and FIG. 9 depicts an exemplary error handling process 900 suitable for implementation by the other of the control modules 512, 520 of the infusion device 502 in conjunction with the error handling process 700 of FIG. 7. For purposes of explanation, but without limitation, the error handling process 800 of FIG. 8 is referred to herein as the master error handling process and the error handling process 900 is referred to herein as the slave error handling process. In exemplary embodiments described herein, the pump control module 520 implements the master error handling process 800 in conjunction with the error handling process 700 of FIG. 7, while the motor control module 512 performs the slave error handling process 900 of FIG. 9; however, it should be appreciated that the subject matter described herein is not necessarily limited to which particular control module 512, 520 is implementing a particular error handling process 800, 900.

Referring first to FIG. 8, the master error handling process 800 initializes or begins by verifying that the error reset limit for the control module 520 has not been met (task 802). In this regard, upon reset or initialization of the pump control module 520, the pump control boot loader 610 accesses the error registers 614 of the internal memory 604 and identifies or otherwise determines whether there is available memory in the error registers 614 for storing diagnostic information for a future anomalous condition. When the boot loader 610 determines the error registers 614 are full, the boot loader 610 automatically operates one or more output user interface elements 540 associated with the pump control module 520 to provide a notification to the patient (task 804), and the master error handling process 800 may terminate or otherwise exit without loading the pump control operating system 612 or application code 620. In this regard, when there is no available internal memory 604 for storing diagnostic information, the boot loader 610 may prevent the operating system 612 or other application code 620 from being executed because diagnostic information for debugging any future anomalous conditions cannot be stored. The pump control boot loader 610 may generate or otherwise provide a graphical user notification on an LCD 540 (e.g., display element 226) of the infusion device 502 that alerts or otherwise notifies the patient that the infusion device 502 requires maintenance and is currently inoperable.

When the master error handling process 800 determines available internal memory exists for future anomalous conditions, the master error handling process 800 continues with the pump control boot loader 610 performing the power-on self-tests or other self-checks to verify that the pump control module 520 is operational and that the operating system 612 may be loaded (task 806). If one or more of the initialization tests performed by the boot loader 610 fail, the boot loader 610 generates or otherwise provides a graphical user notification via a user interface 540 associated with the pump control module 520 (task 804) in a similar manner as described above.

When the initialization tests are all completed successfully or otherwise passed, the master error handling process 800 continues with the pump control boot loader 610 verifying that a handshaking communication has been received from the boot loader 610 executing on the motor control module 512 within a prescribed timeout period (task 808). In this regard, the pump control boot loader 610 may be configured to monitor or otherwise listen for a communication transmitted by the motor control boot loader 610 on the bus (or other interface) communicatively coupling the pump control module 520 to the motor control module 512 for a duration of time corresponding to the timeout period associated with the boot loader handshaking sequence. In other embodiments, the pump control boot loader 610 may be configured to automatically transmit a request or other communication to the motor control module 512 for acknowledgment by the motor control boot loader 610. In the absence of receiving a handshaking communication from the motor control boot loader 610 within a timeout period associated with the boot loader handshaking sequence, the pump control boot loader 610 automatically generates or otherwise provides a user notification (task 804).

Still referring to FIG. 8, when the error reset limit has not been met, the boot loader tests have been performed and completed successfully, and a valid handshake with the boot loader of the other control module has occurred, the master error handling process 800 continues by loading or otherwise executing the operating system (task 810). Thus, the pump control operating system 612 may be loaded by the pump control boot loader 610 only when the pump control module internal memory 604 includes space for diagnostic information for future anomalous conditions, and when it has been verified that both the pump control module 520 is operable and that the motor control module 512 is operable (e.g., by virtue of the successful boot loader handshaking). In exemplary embodiments, when the master error handling process 800 is being performed upon a reset initiated based on the detection of an anomalous condition, the pump control operating system 612 generates or otherwise provides a graphical user notification, for example, via the LCD or other display element 540 associated with the infusion device 502. In this regard, the graphical user notification may indicate that the pump control module 520 has been reset in response to the detection of an anomalous condition or other erroneous state. Additionally, the graphical user notification may include information pertaining to the anomalous condition. For example, the pump control operating system 612 may be configured to access the portion of the error registers 614 including diagnostic information for the most recent anomalous condition, and then generate, based at least in part on that diagnostic information, a graphical user notification that indicates the type of anomalous condition that was detected and/or other pertinent information that may be useful to a user attempting to resolve or otherwise ascertain the severity of the anomalous condition.

After the operating system is loaded, the master error handling process 800 continues by verifying that a handshaking communication has been received from the operating system on the other control module prescribed timeout period (task 812). In this regard, in a similar manner as described above in the context of the boot loader handshaking, the pump control operating system 612 may be configured to monitor or otherwise listen for a communication transmitted by the motor control operating system 612 for a duration of time corresponding to the timeout period associated with the operating system handshaking sequence. Alternatively, the pump control operating system 612 may automatically transmit a request or other communication to the motor control module 512 for acknowledgment by the motor control operating system 612. Again, in the absence of receiving a handshaking communication from the motor control operating system 612 within a timeout period associated with the operating system handshaking sequence, the pump control operating system 612 automatically generates or otherwise provides a user notification (task 804). In this regard, the pump control operating system 612 does not proceed with loading application code 620 from the external memory 622 until verifying that the motor control operating system 612 is executing on the motor control module 512 and functioning normally or as intended in the context of the error handling process 700.

When a successful handshake is performed between the operating systems executing on the control modules 512, 520, the master error handling process 800 continues by saving diagnostic information for a preceding anomalous condition when is being performed upon a reset initiated based on the detection of the anomalous condition, and loading or otherwise executing the more complex application code that dictates the infusion device delivery operations (task 814). In this regard, the pump control operating system 612 may retrieve or otherwise obtain the diagnostic information for the most recent anomalous condition from the error registers 614 and generate a corresponding file containing the diagnostic information, which, in turn, is then transferred from the pump control module 520 for long term storage. For example, the pump control operating system 612 may create a dump file corresponding to the preceding anomalous condition, and then write the dump file to the external memory 622 or upload the dump file to a remote server or the like via a communications interface coupled to the pump control module 520. Additionally, the pump control operating system 612 accesses the external memory 622 to retrieve or otherwise obtain the delivery control application code 620 (e.g., closed-loop operating mode application code or the like) for execution by the processing core 602 to support generating delivery commands for operating the motor 507 to deliver fluid to the patient, as described above.

During execution of the application(s), the master error handling process 800 detects or otherwise identifies an anomalous condition or erroneous state, and in response, performs one or more error processing operations and verifies that the diagnostic information pertaining to the anomalous condition has been written or otherwise stored to the control module's internal memory before resetting the control module (tasks 816, 818, 820, 822). In one or more embodiments, the pump control operating system 612 continually monitors or otherwise listens for a periodic heartbeat message from the motor control operating system 612 that verifies or otherwise indicates that the motor control module 512 is functioning normally, and the pump control operating system 612 automatically detects or otherwise identifies an anomalous condition with respect to the motor control module 512 in response to a failure to receive the heartbeat message from the motor control module 512 within the heartbeat period. In some embodiments, the pump control operating system 612 may also detect an anomalous condition with respect to the motor control module 512 in response to receiving an indication from the motor control module 512 that the motor control module has detected an anomalous condition. Additionally, the pump control operating system 612 may detect or otherwise identify anomalous conditions with respect to the pump control module 520, for example, in response to detecting an address of the memory 622 that the processing core 602 is attempting to access is corrupted or invalid. In this regard, the application 620 may notify the operating system 612 of an anomalous condition or potential erroneous state when an exception encountered during execution of the application code 620 cannot be handled by the exception handling associated with the application code 620.

In exemplary embodiments, the error processing operations performed by the pump control operating system 612 include disabling or otherwise deactivating any interrupts that may be generated by the pump control module 520 and disabling input power to the motor 507 by opening, turning off, or otherwise deactivating the switching arrangement 513. Additionally, the pump control operating system 612 stops further execution of any instructions, tasks, or operations associated with the pump control operating system 612 as well as those associated with the application code 620. Thereafter, the pump control operating system 612 stores or otherwise maintains the diagnostic information corresponding to the current state of the processing core 602 to the error registers 614, for example, by storing or otherwise writing the current line-of-execution, the data or values stored in pipeline registers, the current call stack, and the like. The pump control operating system 612 verifies or otherwise validates that the diagnostic information corresponding to the current state of the processing core 602 was successfully stored or written to the error registers 614, and in response to a failure to store the diagnostic information in the internal memory 604, the pump control operating system 612 maintains the processing core 602 in its halted state and generates or otherwise provides a user notification that indicates that the infusion device 502 requires maintenance or assistance (task 804).

After verifying that the diagnostic information has been successfully stored to the internal memory 604, the pump control operating system 612 resets the pump control module 520 by transferring or otherwise loading the boot loader code 610 into the processing core 602 for execution. Upon execution, the boot loader 610 initially verifies that the error reset limit for the pump control module 520 has not been met (task 802) before repeating the steps of performing initialization tests and verifying a handshake with the motor control boot loader 610 before reloading the pump control operating system 612 (tasks 806, 808, 810), thereby repeating the master error handling process 800. In this regard, upon reset of the pump control module 520, when the pump control boot loader 610 identifies that the diagnostic information for the most recent anomalous condition has resulted in the error registers 614 becoming full, the pump control boot loader 610 determines that the error reset limit has been met, generates a user notification indicating that the infusion device 502 requires maintenance or other attention, and disables further loading of the operating system code 612 or the application code 620 into the pump control processing core 602.

Referring now to FIG. 9, the slave error handling process 900 initializes or begins by performing the power-on self-tests or other self-checks to verify that the motor control module 512 is operational (task 902). The motor control boot loader 610 performs initialization tests to verify valid operation of the motor control module 512 may be achieved, and when one or more of the initialization tests performed by the motor control boot loader 610 fail, the motor control boot loader 610 generates or otherwise provides a user notification via a user interface 540 associated with the motor control module 512 (task 904). In this regard, the motor control boot loader 610 may illuminate a LED 540 and/or a haptic output element 540 coupled to the motor control module 512 that different from the output user interface element(s) 540 utilized by the pump control module 520 when generating alerts in conjunction with the error handling process 700, thereby indicating that the motor control module 512 requires maintenance or attention.

When the initialization tests are all completed successfully or otherwise passed, the slave error handling process 900 continues with the motor control boot loader 610 verifying that a handshaking communication has been received from the pump control boot loader 610 executing on the pump control module 520 within a prescribed timeout period (task 906). In this regard, motor control boot loader 610 may automatically transmit or otherwise provide one or more communications on the bus (or other interface) communicatively coupling the pump control module 520 to the motor control module 512 that indicate that the boot loader 610 on the motor control module 512 is ready to load the motor control operating system 612. The motor control boot loader 610 may be configured to monitor or otherwise listen for a corresponding communication transmitted by the pump control boot loader 610 within a timeout period associated with the boot loader handshaking sequence that indicates that the pump control boot loader 610 is also concurrently executing and ready to load the pump control operating system 612. In a similar manner as described above in the context of FIG. 8, in the absence of receiving a handshaking communication from the pump control boot loader 610 within a timeout period associated with the boot loader handshaking sequence, the motor control boot loader 610 automatically generates or otherwise provides a user notification (task 904) and the slave error handling process 900 may exit or terminate.

After a successful boot loader handshake, the slave error handling process 900 continues with the motor control boot loader 610 loading the motor control operating system code 612 into the processing core 602 for execution (task 908). Thereafter, the motor control operating system 612 verifies that the error reset limit for the motor control module 512 has not been met (task 910). In this regard, the motor control operating system 612 accesses the error registers 614 of the motor control internal memory 604 and identifies or otherwise determines whether there is available memory in the error registers 614 for storing diagnostic information for a future anomalous condition. In a similar manner as described above, when the boot loader 610 determines the error registers 614 are full, the motor control boot loader 610 automatically operates one or more output user interface elements 540 associated with the motor control module 512 to provide a notification to the patient (task 904).

When the slave error handling process 900 determines available internal memory exists for future anomalous conditions, the slave error handling process 900 continues by verifying that a handshaking communication has been received from the operating system on the other control module within a prescribed timeout period (task 912). In this regard, the motor control operating system 612 may be configured to automatically transmit or otherwise provide a communication to the pump control module 520 that indicates that the motor control module operating system 612 has verified the error limit has not been met and that the motor control module 512 is ready to execute its associated application code 620 in memory 622. Thereafter, the motor control operating system 612 may be configured to monitor or otherwise listen for a communication transmitted by the pump control operating system 612 that confirms that the pump control operating system 612 is concurrently executing and ready to load its associated application code 620 from memory 622. Again, in the absence of receiving a handshaking communication from the pump control operating system 612 within a timeout period associated with the operating system handshaking sequence, the motor control operating system 612 may automatically generate or otherwise provide a user notification (task 904) and terminate the slave error handling process 900.

After a successful operating system handshake, the slave error handling process 900 continues by transferring the motor control module diagnostic information to the pump control module and executing the application code associated with the motor control module (task 914). In this regard, in one or more embodiments, when the slave error handling process 900 is being performed upon a reset initiated based on the detection of the anomalous condition, the motor control operating system 612 automatically retrieves or otherwise obtains the diagnostic information for the most recent anomalous condition from the error registers 614, and then transmits or otherwise provides the diagnostic information to the pump control operating system 612. Thereafter, the pump control operating system 612 may generate a corresponding file that contains the received motor control module diagnostic information, which, in turn, is then transferred from the pump control module 520 for long term storage. In some embodiments, a dump file created by the pump control operating system 612 may include diagnostic information obtained from the motor control module 512 for the most recent anomalous condition along with the diagnostic information corresponding to the preceding anomalous condition from the pump control error registers 614. The pump control operating system 612 assumes responsibility of writing the dump file including the motor control module diagnostic information to the external memory 622 or uploading the dump file to a remote server or the like. Additionally, the motor control operating system 612 accesses the external memory 622 to retrieve or otherwise obtain the motor control application code 620 for execution by the processing core 602 to support converting delivery commands received from the pump control module 520 into corresponding motor commands for operating the motor driver module 514 to deliver fluid to the patient, as described above.

In a similar manner as described above in the context of FIG. 8, the slave error handling process 900 continues with the motor control operating system 612 detecting or otherwise identifying an anomalous condition, and in response, performing one or more error processing operations and verifying that diagnostic information pertaining to the anomalous condition has been written or otherwise stored to the control module's internal memory before resetting the control module (tasks 916, 918, 920, 922). In one or more embodiments, the pump control operating system 612 continually monitors or otherwise listens for an acknowledgment sent by the pump control operating system 612 in response to a periodic heartbeat message transmitted by the motor control operating system 612, which, in turn, verifies or otherwise indicates that the pump control module 520 is functioning normally. In such embodiments, the motor control operating system 612 may automatically detect or otherwise identify an anomalous condition with respect to the pump control module 520 in response to a failure to receive a heartbeat acknowledgment from the pump control module 520 within a prescribed time period. In some embodiments, the motor control operating system 612 may also detect an anomalous condition with respect to the pump control module 520 in response to receiving an indication from the pump control module 520 that the pump control module 520 has detected an anomalous condition. Additionally, the motor control operating system 612 may detect or otherwise identify anomalous conditions with respect to the motor control module 512, for example, in response to detecting the motor control processing core 602 is attempting to access a corrupted or invalid address in the memory 622. In this regard, the motor control application 620 may notify the motor control operating system 612 of an anomalous condition or potential erroneous state when an exception encountered during execution of the motor control application code 620 cannot be handled by the exception handling associated with the motor control application code 620.

In exemplary embodiments, the error processing operations performed by the motor control operating system 612 include disabling or otherwise deactivating any interrupts that may be generated by the motor control module 512 and disabling input power to the motor 507 by opening, turning off, or otherwise deactivating the switching arrangement 515. Additionally, the motor control operating system 612 stops further execution of any instructions, tasks, or operations associated with the motor control operating system 612 as well as those associated with the motor control application code 620. Thereafter, the motor control operating system 612 stores or otherwise maintains the diagnostic information corresponding to the current state of the motor control processing core 602 to its internal error registers 614, for example, by storing or otherwise writing the current line-of-execution, the data or values stored in pipeline registers, the current call stack, and the like. The motor control operating system 612 verifies or otherwise validates that the diagnostic information corresponding to the current state of the processing core 602 was successfully stored or written to the error registers 614, and in response to a failure to store the diagnostic information in the internal memory 604, the motor control operating system 612 maintains the processing core 602 in its halted state and generates or otherwise provides a user notification that indicates that the infusion device 502 requires maintenance or assistance (task 904).

After verifying that the diagnostic information has been successfully stored to the internal memory 604, the motor control operating system 612 resets the motor control module 512 by transferring or otherwise loading the motor control boot loader code 610 into the processing core 602 for execution. Upon execution, the motor control boot loader 610 performs initialization tests and verifies a handshake with the pump control boot loader before reloading the motor control operating system 612 (tasks 902, 906, 908), thereby repeating the slave error handling process 900. In this regard, upon reset of the motor control module 512, when the motor control operating system 612 identifies that the diagnostic information for the most recent anomalous condition has resulted in the motor control error registers 614 becoming full, the motor control boot loader 610 determines that the error reset limit has been met, generates a user notification indicating that the infusion device 502 requires maintenance or other attention, and disables further loading of the motor control application code 620 into the motor control processing core 602. In this manner, the motor control module 512 provides redundancy in the event of unsynchronized errors or other unpredictable error sequences that result in the motor control module 512 reaching the error reset limit without the pump control boot loader 610 realizing the error reset limit has been met.

To briefly summarize, the subject matter describes herein distributes motor control across control modules (or processors) of the infusion device in a manner that enhances safety by allowing any of the control modules to unilaterally and/or redundantly detect anomalous conditions and stop delivery by removing input power to the motor. Additionally, each control module may automatically generate alerts independently of the other control module to ensure that the patient or other user is notified of any potential problems, for example, when a successful dump of the diagnostic information for an anomalous state cannot be verified or when the number of resets performed in response to anomalous conditions exceeds an allowable reset limit. In exemplary embodiments, upon initial power on or a reset, the control modules establish handshakes so that the progress substantially concurrently from the boot loader stage, to the operating system stage, and ultimately to the application stage, during which heartbeat messages or other communications are utilized to verify both control modules are functioning normally. Thus, not only may a control module that detects an anomalous condition automatically reset itself to the known stable boot loader stage, but the other control module may identify the anomalous condition with respect to the first control module based on the communications with the first control module (e.g., an absence of a heartbeat message or heartbeat acknowledgment) and automatically store its diagnostic information and reset to the known stable boot loader stage to repeat the handshaking and other self-diagnostics or performance verification tests before complex applications are re-executed by the control modules. In this manner, the control modules cooperate to deterministically respond to anomalous conditions in a manner that provides redundancy while ensuring that diagnostic information for analyzing the anomalous conditions is maintained and user notifications are generated as appropriate.

For the sake of brevity, conventional techniques related to booting, exception handling or other error handling or processing, glucose sensing and/or monitoring, closed-loop glucose control, closed-loop motor control, sensor calibration and/or compensation, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. An infusion device comprising:
a motor operable to deliver fluid to a body of a user;
a first control module to enable input power for the motor and provide a dosage command for operating the motor; and
a second control module coupled to the first control module to receive the dosage command and operate the motor using at least a portion of the input power based at least in part on the dosage command, wherein one of the first control module and the second control module:
  detects an anomalous condition in response to an absence of a communication from the other of the first control module and the second control module; and
  in response to the anomalous condition:
    disconnects the motor from the input power;
    stores diagnostic information for the anomalous condition in an internal memory of the one of the first control module and the second control module; and
    after disabling the input power and storing the diagnostic information, reinitializes a processing core of the one of the first control module and the second control module to execute boot loader code.

2. The infusion device of claim 1, further comprising a driver module coupled to the motor, wherein:
the first control module enables the input power to the driver module; and
the second control module operates the driver module to deliver the portion of the input power to the motor in accordance with the dosage command.

3. The infusion device of claim 1, wherein a first operating system executing on the one of the first control module and the second control module detects the anomalous condition in response to the absence of the communication from a second operating system executing on the other of the first control module and the second control module.

4. The infusion device of claim 1, wherein the other of the first control module and the second control module:
detects the anomalous condition in response to an absence of a second communication from the one of the first control module and the second control module; and
in response:
  stores second diagnostic information for the anomalous condition in its internal memory; and
  resets after storing the second diagnostic information.

5. The infusion device of claim 1, further comprising an output user interface element coupled to the one of the first control module and the second control module, wherein the one of the first control module and the second control module verifies the diagnostic information for the anomalous condition is stored in the internal memory prior to reinitializing the processing core and generates a notification via the output user interface element in response to a failure to store the diagnostic information.

6. The infusion device of claim 1, further comprising an output user interface element coupled to the one of the first control module and the second control module, the processing core of the one of the first control module and the second control module executing the boot loader code for a first boot loader, wherein the one of the first control module and the second control module generates a notification via the output user interface element in response to a failure to communicate with a second boot loader executed by the other of the first control module and the second control module.

7. The infusion device of claim 1, the second control module converting the dosage command to one or more motor commands for providing the input power to the motor, wherein the anomalous condition comprises an absence of a heartbeat message of one or more heartbeat messages communicated between the first control module and the second control module.

8. The infusion device of claim 7, wherein in response to the anomalous condition:
the other of the first control module and the second control module stores second diagnostic information for the anomalous condition from its processing core to its internal memory; and
after storing the second diagnostic information, the other of the first control module and the second control module loads second boot loader code from its internal memory to its processing core.

9. The infusion device of claim 8, wherein the anomalous condition results in the other of the first control module and the second control module failing to communicate the heartbeat message.

10. The infusion device of claim 7, further comprising an output user interface element, wherein:
the one of the first control module and the second control module verifies the storing of the diagnostic information prior to loading the boot loader code; and
the one of the first control module and the second control module generates a notification via the output user interface element in response to a failure to store the diagnostic information.

11. The infusion device of claim 7, further comprising an output user interface element, wherein the one of the first control module and the second control module generates a notification via the output user interface element when a reset limit has been met.

12. An infusion device comprising:
a motor operable to deliver fluid to a body of a user;
a first control module to enable input power for the motor and provide a dosage command for operating the motor; and
a second control module coupled to the first control module to receive the dosage command and operate the motor using at least a portion of the input power based at least in part on the dosage command, wherein:
the first control module and the second control module are cooperatively configured to:
  initialize each of the first control module and the second control module to a boot loader stage;
  in response to a first handshake between the first control module and the second control module while in the boot loader stage, load a respective operating system for execution by each of the first control module and the second control module; and
  in response to a second handshake between the respective operating systems executing on the first control module and the second control module, load respective application code for execution by each of the first control module and the second control module from external memory; and
one of the first control module and the second control module:

detects an anomalous condition in response to an absence of a communication from the other of the first control module and the second control module; and in response to the anomalous condition:
disables the input power to the motor;
stores diagnostic information for the anomalous condition in its internal memory; and
resets after disabling the input power and storing the diagnostic information.

13. The infusion device of claim 12, wherein:
the first control module detects the anomalous condition after loading first application code for execution by the first control module from the external memory; and
in response to the anomalous condition the first control module disables the input power to the motor, stores the diagnostic information for the anomalous condition from its processing core to its internal memory, and resets to the boot loader stage after storing the diagnostic information.

14. The infusion device of claim 13, wherein:
the second control module identifies the anomalous condition in response to the first control module detecting the anomalous condition; and
in response to identifying the anomalous condition, the second control module stores second diagnostic information for the anomalous condition from its processing core to its internal memory and resets to the boot loader stage after storing the second diagnostic information.

15. The infusion device of claim 12, wherein the one of the first control module and the second control module determines whether a reset limit has been met at the boot loader stage prior to the first handshake.

16. The infusion device of claim 15, wherein the respective operating system executing on the other of the first control module and the second control module determines whether the reset limit has been met prior to the second handshake.

17. The infusion device of claim 12, wherein loading respective application code for execution by each of the first control module and the second control module from the external memory comprises:
executing, by the first control module, a delivery control application for determining a dosage command corresponding to an amount of fluid for delivery to a user associated with the infusion device; and
executing, by the second control module, a motor control application for converting the dosage command to one or more motor commands for operating the motor to deliver the amount of fluid.

18. The infusion device of claim 17, wherein the first control module detects the anomalous condition after providing the dosage command to the second control module.

19. The infusion device of claim 17, wherein the second control module detects the anomalous condition after receiving the dosage command from the first control module.

\* \* \* \* \*